(12) United States Patent
Bannasch et al.

(10) Patent No.: US 8,333,417 B2
(45) Date of Patent: Dec. 18, 2012

(54) MANIPULATOR TOOL AND HOLDING AND/OR EXPANDING TOOL WITH AT LEAST ONE MANIPULATOR TOOL

(75) Inventors: Rudolf Bannasch, Berlin (DE); Leif Kniese, Berlin (DE)

(73) Assignee: Karl Storz GmbH & Co. KG, Tuttlingen (DE)

(*) Notice: Subject to any disclaimer, the term of this patent is extended or adjusted under 35 U.S.C. 154(b) by 248 days.

(21) Appl. No.: 12/762,962

(22) Filed: Apr. 19, 2010

(65) Prior Publication Data

US 2010/0263500 A1  Oct. 21, 2010

(30) Foreign Application Priority Data

Apr. 19, 2009 (DE) .......................... 10 2009 017 591

(51) Int. Cl.
*B25J 15/12* (2006.01)
(52) U.S. Cl. .................... 294/100; 294/99.1; 606/206
(58) Field of Classification Search ................ 294/99.1, 294/99.2, 100, 111, 196; 606/206, 207
See application file for complete search history.

(56) References Cited

U.S. PATENT DOCUMENTS

| | | | | |
|---|---|---|---|---|
| 2,545,452 A | * | 3/1951 | Fletcher | 623/64 |
| 2,549,257 A | * | 4/1951 | Staunt | 294/19.2 |
| 3,527,492 A | * | 9/1970 | Hollis | 294/115 |
| 4,719,826 A | | 1/1988 | DuBois | |
| 5,356,187 A | * | 10/1994 | McCarthy et al. | 294/99.1 |
| 5,522,290 A | * | 6/1996 | Visser et al. | 81/427 |
| 5,964,780 A | | 10/1999 | Balazs | |
| 8,156,995 B2 | * | 4/2012 | Kniese | 160/352 |
| 2004/0026942 A1 | * | 2/2004 | Kessler et al. | 294/100 |
| 2004/0183348 A1 | | 9/2004 | Kniese | |

FOREIGN PATENT DOCUMENTS

| | | |
|---|---|---|
| DE | 19537320 | 4/1997 |
| DE | 20318845 | 3/2004 |
| DE | 102005010380 | 9/2006 |
| DE | 102006009559 | 5/2007 |
| DE | 102007026721 | 5/2008 |
| FR | 545837 | 10/1922 |
| WO | 2009039231 | 3/2009 |

* cited by examiner

*Primary Examiner* — Dean Kramer
(74) *Attorney, Agent, or Firm* — Mark P. Stone

(57) ABSTRACT

One or more embodiments of a flexible manipulator tools are provided. The flexible manipulator tool can include a distal end movable in at least one manipulation plane with respect to a proximal end. The flexible manipulator tool can also include at least two cheeks extending side by side to and spaced apart from each other.

14 Claims, 27 Drawing Sheets

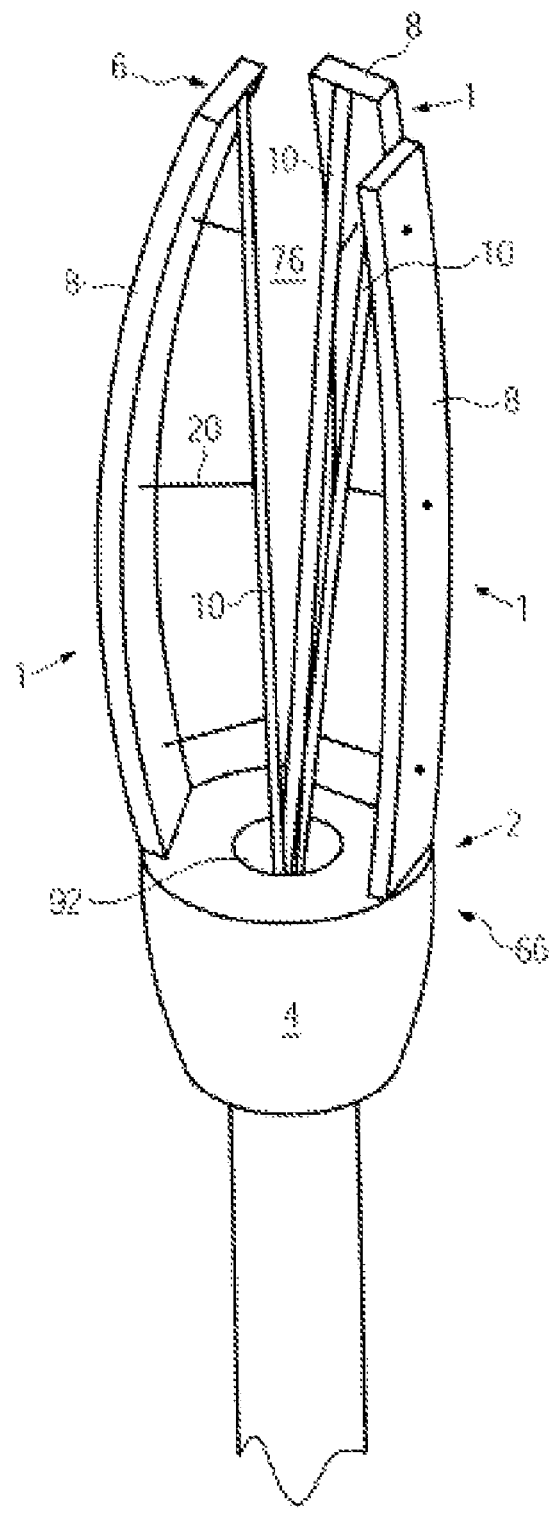
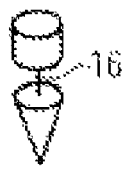
FIG. 23

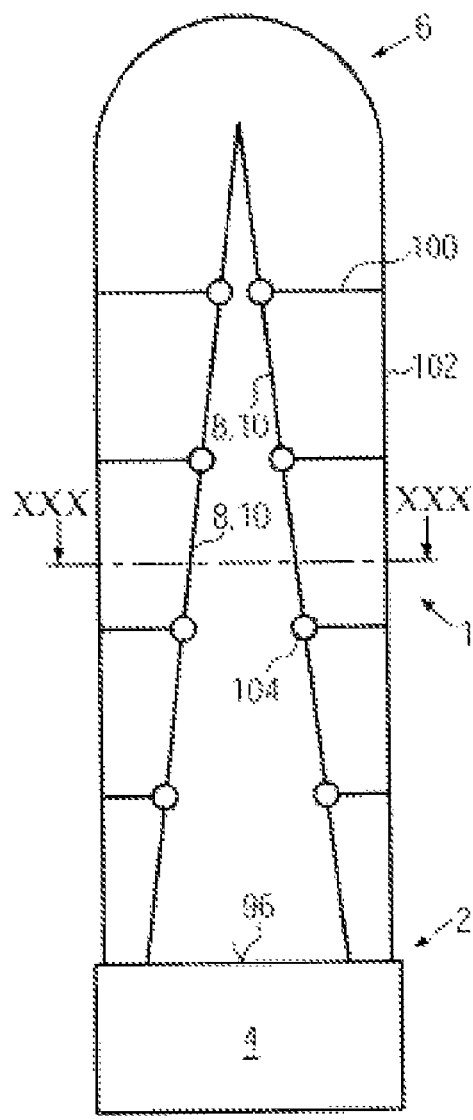
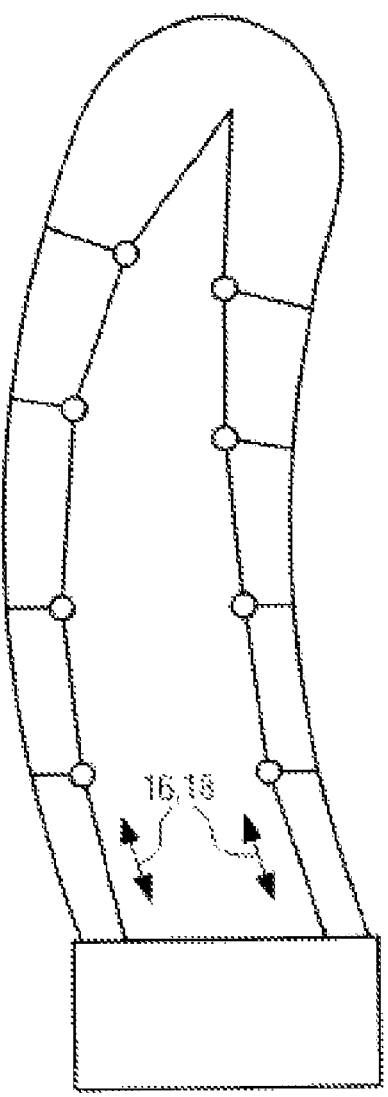
FIG. 28  FIG. 29
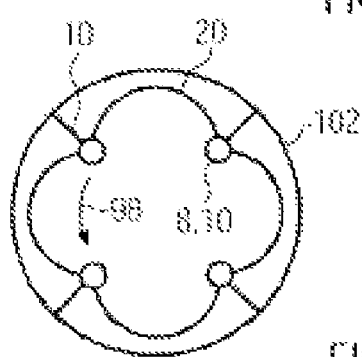
FIG. 30

MANIPULATOR TOOL AND HOLDING AND/OR EXPANDING TOOL WITH AT LEAST ONE MANIPULATOR TOOL

CROSS REFERENCE TO RELATED APPLICATION

The present application claims priority and the benefit of co-pending German Patent Application No. 102009017591.1 filed on Apr. 19, 2009, entitled "MANIPULATOR TOOL AND HOLDING AND/OR EXPANDING TOOL WITH AT LEAST ONE MANIPULATOR TOOL", which is incorporated in its entirety herein.

FIELD

The present embodiments relate to a flexible manipulator tool.

BACKGROUND

A need exists for a flexible manipulator tool with an increased number of possible applications.

Typical manipulator tools are disclosed in DE-A-199164111 as well as EP-A-1040999 and EP-A-1316651. The manipulator tools disclosed in the above references can be used with tongs as disclosed by EP-A-1203640. However, the manipulator tools applications are limited.

Therefore, a need exists for an efficient configuration of a manipulator tool that increases the applications or uses of the manipulator tool.

The present embodiments meet these needs.

BRIEF DESCRIPTION OF THE DRAWINGS

The detailed description will be better understood in conjunction with the accompanying drawings as follows:

FIG. 23 depicts a schematic representation of a further embodiment of a holding and/or expanding tool according to the invention.

FIG. 28 depicts a schematic representation of a further embodiment of a manipulator tool according to the invention, in particular for endoscopic applications;

FIG. 29 depicts a schematic representation of the embodiment of FIG. 28 in a deflected position.

FIG. 30 depicts a schematic representation of a sectional view along line XXX-XXX of FIG. 28.

Figure 1:
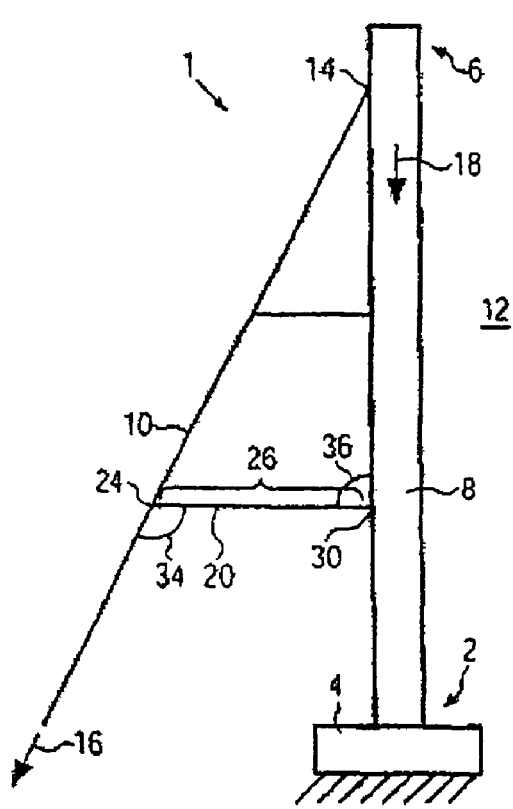
FIG. 1 depicts a schematic representation of a first embodiment of the manipulator tool according to the invention in an original position.

The present embodiments are detailed below with reference to the listed Figures.

DETAILED DESCRIPTION OF THE EMBODIMENTS

Before explaining the present apparatus in detail, it is to be understood that the apparatus is not limited to the particular embodiments and that it can be practiced or carried out in various ways.

The present embodiments relate to a manipulator tool.

In the following description of the embodiments according to the invention, the same reference numerals are used for components corresponding to each other with respect to function and/or shape. To keep the description short, only distinguishing features with respect to the other embodiments are discussed for the individual embodiments, wherein the distinguishing features of different embodiments can be combined with each other.

One or more embodiments of a manipulator tool are depicted in FIG. 1. Referring now to FIG. 1, a manipulator tool 1 is fixed at a proximal end 2 to a tool base 4. The tool base, which is only shown schematically, can be a tool holder or a housing. A distal end 6 of the manipulator tool 1 is freely movable.

The manipulator tool 1 can include two jaws or cheeks 8 and 10. The first cheek 8 can be resistant to bending and flexurally rigid or stiff. The second cheek 10 can be tension-proof. The second cheek 10 can be formed of a limp traction means. For example, the second cheek 10 can be formed by a rope, a belt, a band, a chain, or similar device or apparatus.

Both cheeks 8 and 10 can be flexible in the manipulation plane 12, which corresponds to the plane of projection in FIG. 1. Accordingly, the manipulator tool 1 can be flexible. The at least first cheek 8 can function as a spring element.

The two cheeks 8 and 10 can be spaced apart at the proximal end 2 and connected to each other at the distal end 6. The connection 14 of the two cheeks 8 and 10 can allow introduction of a pulling force 16 prevailing in the second cheek 10 into the first cheek 8.

Between their respective ends at the proximal end 2 and the connection point 14 at the distal end 6, the two cheeks 8, 10 extend one next to the other at a wedge-shaped angle of less than 90 degrees, so that the pulling force 16 results in a compressive force 18 in the at least flexurally stiff cheek via the connection 14.

One or more at least tension-proof hinge element 20 can be disposed between the proximal end 2 and the distal end 6. The at least tension-proof hinge element 20 can connect the two cheeks 8 and 10 with each other. In one or more embodiments, a plurality of hinge elements can be provided. The at least tension-proof hinge element 20 can be hinged or connected to the first cheek 8, the second cheek 10, or both. The at least tension-proof hinge element 20 can have sufficient flexibility to follow the shear movement. In one or more embodiments, the at least tension-proof hinge element 20 can be limp.

Though basically each of the two cheeks 8 and 10 can be embodied to be tension-proof as well as flexurally stiff independently of each other, this generally involves a higher weight of the manipulator tool compared to a design which takes into consideration the forces occurring in the cheeks 8 and 10 in operation.

Figure 2:
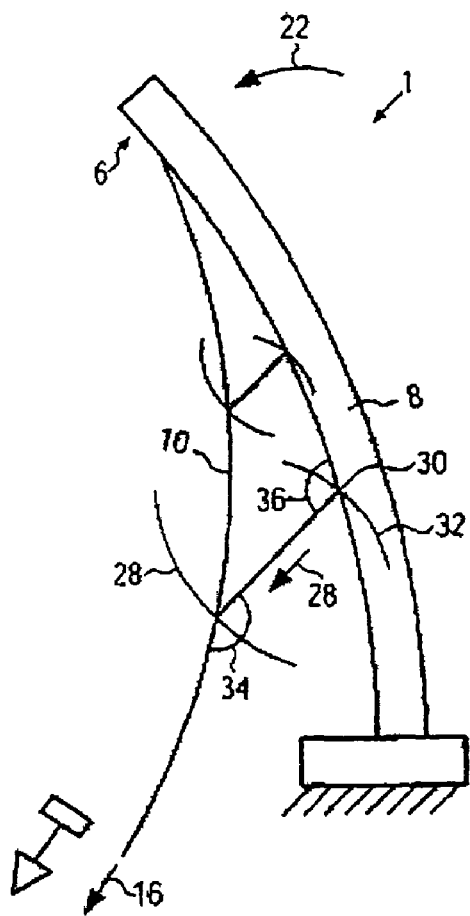
FIG. 2 depicts a schematic representation of the embodiment of FIG. 1 in a deformed position.

With reference to FIGS. 1 and 2, now the function of the manipulator tool 1 according to the invention will be described.

In the embodiment of FIG. 1, the second cheek 10 can be held at the proximal end 2 to be movable lengthwise. If a pulling force 16 is introduced into the cheek 10, the cheek moves in its longitudinal direction towards the proximal end 2 and away from the distal end 6, and the pulling force 16 bends the distal end 6 into its direction, as is indicated by arrow 22 in FIG. 2.

In the course of the deformation, the mounting point 24 moves on an orbit 28 determined by the length 26 of the hinge element 20 around the mounting point 30 of the hinge element 20 at the at least flexurally stiff cheek. Vice-versa, the mounting point 30 of course also moves along an orbit 32 around the anchorage point 24. By changing the length 26 and the angle 34 and 36 between the hinge element 20 and the cheeks 8 and 10 in the basic construction, the deformation geometry of the manipulator tool can be influenced.

The cheeks 8 and 10 can be connected via the at least one hinge element 20, such that they permit shear movements with respect to each other, that means a relative movement between the two cheeks in their longitudinal direction from the proximal to the distal end 2, 6 is possible. This shear movement shows in the change of the angles 34, 36 in the course of the deformation.

The longitudinal movement of the cheek 10, which causes the deformation of the manipulator tool, can be effected in many ways. For example, the first cheek 8 can continue in pulling means guided over a driven winding roller.

If the pulling force decreases, the manipulator tool assumes the rest position again due to the spring action of the first cheek 8.

Figure 3:
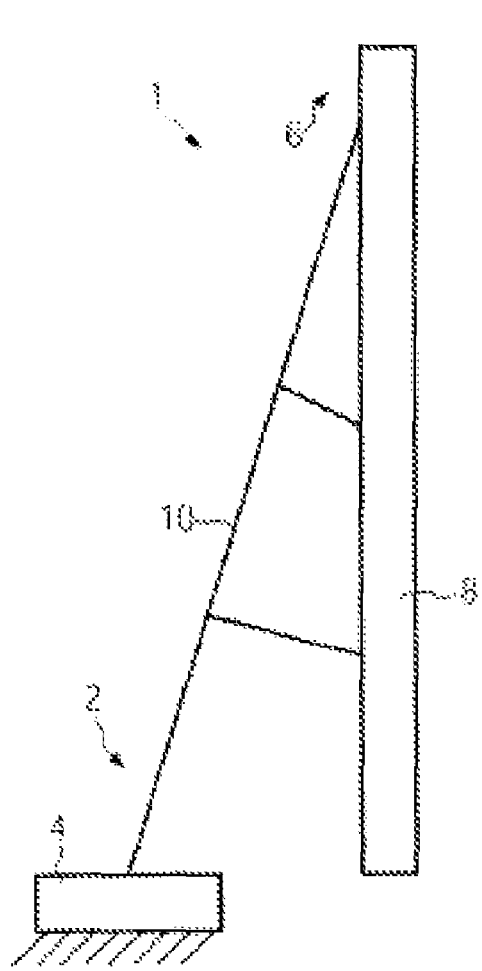
FIG. 3 depicts a further embodiment of the manipulator tool according to the invention in an original position.
Figure 4:
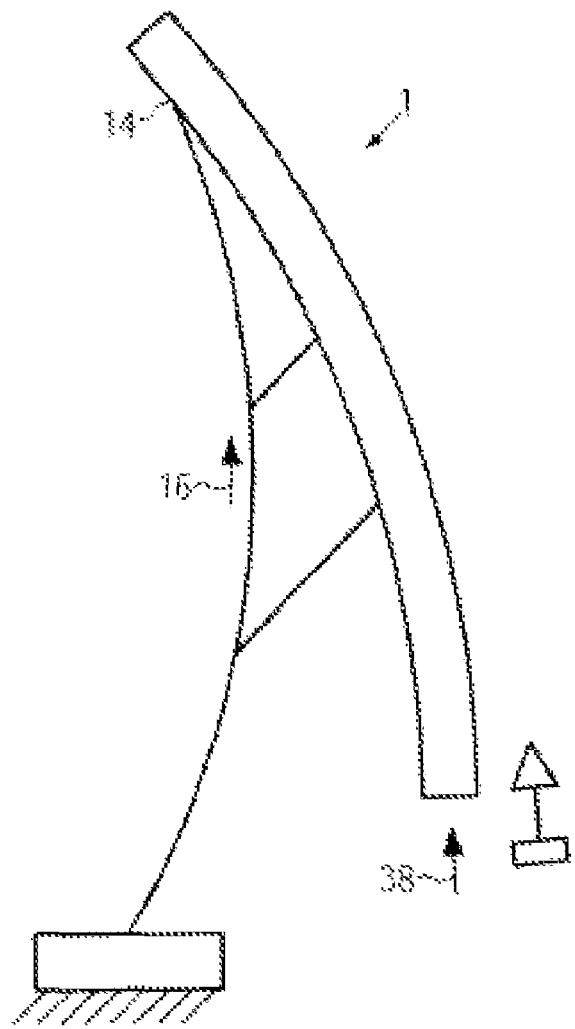
FIG. 4 depicts the embodiment of FIG. 3 in a schematic representation of a deformed position.

A modification of the embodiment of FIGS. 1 and 2 is shown in FIGS. 3 and 4.

In contrast to the embodiment of FIGS. 1 and 2, the first cheek 8 is configured to be lengthwise movable in the embodiment of FIGS. 3 and 4, while the second cheek 10 is fixed at the distal end 6, for example via the tool base 4. A compressive force 38 can be introduced into the second cheek 10 to deform the manipulator tool 1. This can result, via the connection 14, in a pulling force 16 in the second cheek 10.

Figure 5:
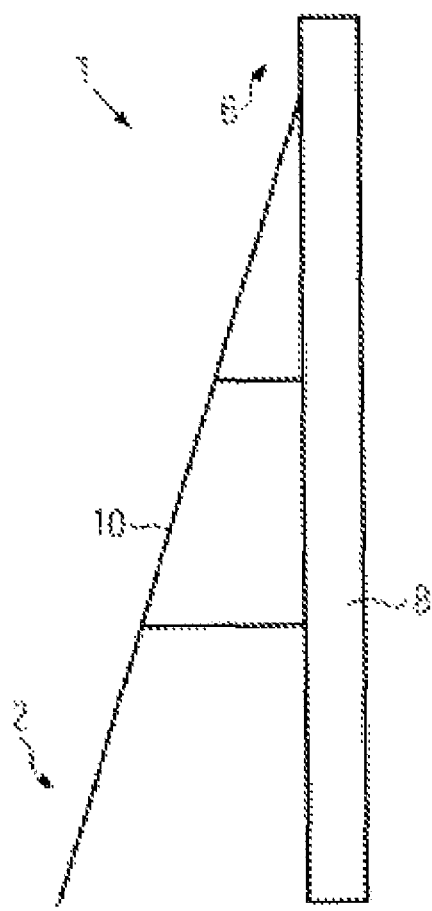
FIG. 5 depicts a schematic representation of a further embodiment of the manipulator tool according to the invention in an original position.
Figure 6:
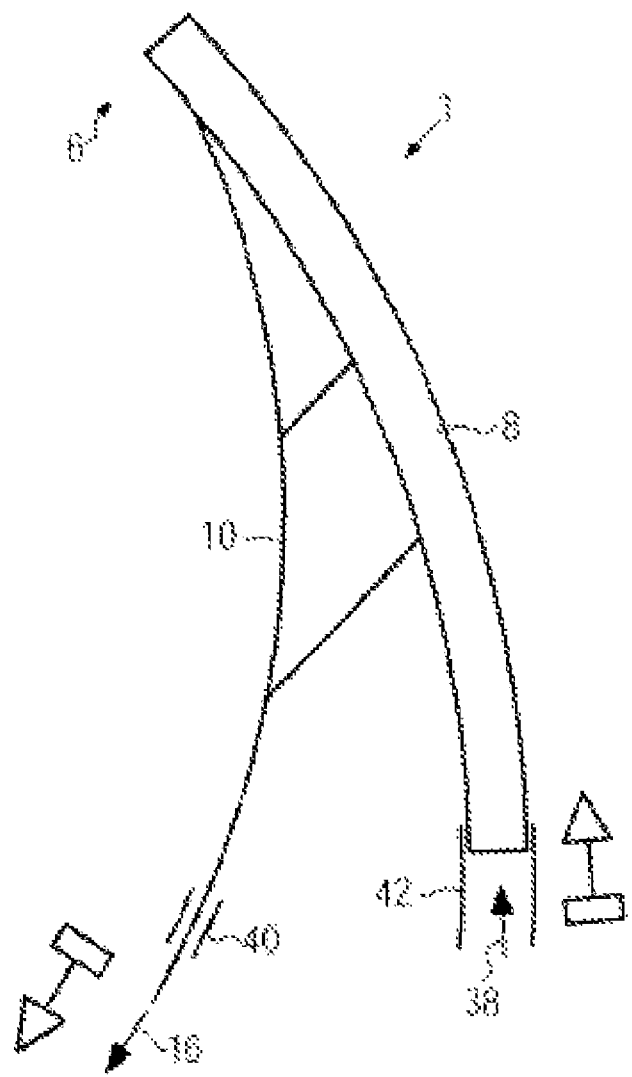
FIG. 6 depicts the embodiment of FIG. 5 in a schematic representation of a deformed position.

Another embodiment of the manipulator tool 1 according to the invention is shown in FIGS. 5 and 6. The embodiment of FIGS. 5 and 6 is mounted to be floating at the proximal end 2, so that a compressive force 38 can be introduced into the first cheek 8, and simultaneously a pulling force can be introduced into the second cheek 10.

If one of the two cheeks 8 and 10 is fixed and only the other cheek 10 and 8 is moved, the embodiments of FIGS. 1 and 2 (if the first cheek 8 is fixed) or FIGS. 3 and 4 (if the second cheek 10 is fixed) result again.

To avoid the introduction of moments into the cheeks 8 and 10 and to introduce a mere compressive force 38 into the first cheek 8 and a mere pulling force 16 into the second cheek 10, linear guides 40 and 42 can be provided which guide the respective cheek 8 and 10 in a straight line in their longitudinal direction.

If both cheeks 8 and 10 are tension-proof as well as stiff in compression, or if both cheeks are flexurally stiff, one cheek can be fixed to the tool base 4 at the proximal end 2, and both a pulling force 16 and a compressive force 38 can be introduced into the other cheek, so that a deformation of the flexible manipulator tool can be achieved with the curvature or bend shown in FIG. 4 as well as with the bend opposite thereto.

Naturally, the complete manipulator tool 1 can also be held at the tool base 4 to be lengthwise movable or swiveling.

In the above embodiments, the manipulator tool 1 can be employed in particular as tool carrier. This will be briefly described with reference to the embodiments of FIGS. 7 to 10.

Figure 7:
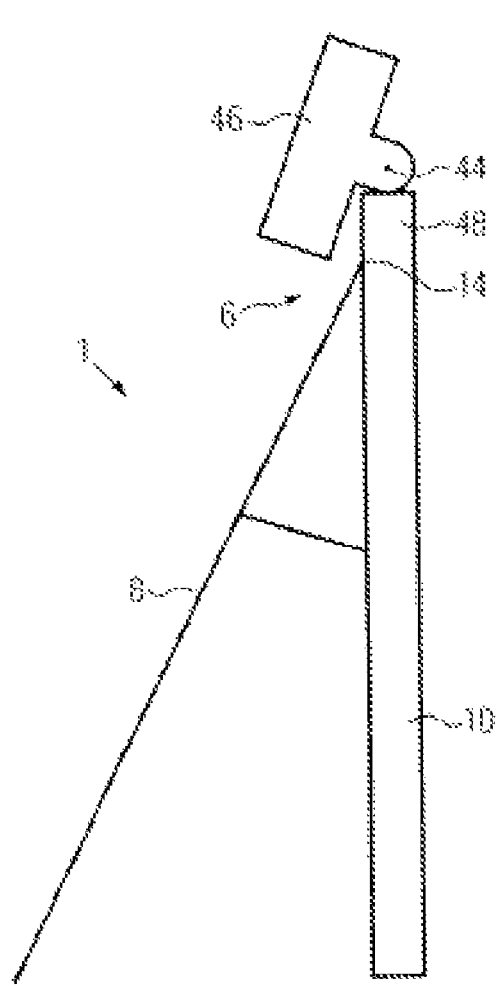
FIG. 7 depicts a schematic representations of various embodiments of a distal end of the manipulator tool according to the invention.

In the embodiment of FIG. 7, a tool holder 44 which can carry a tool 46 is attached to the distal end 6.

As is shown in FIG. 7, the tool holder 44 can be attached to a section 48 continued via the connection point 14 of the two cheeks 8 and 10, hereinafter referred to as extension. In the movement 22 (FIG. 2) of the manipulator tool 1, the tool 46 can be placed so as to contact a workpiece which is not shown here.

Figure 8:
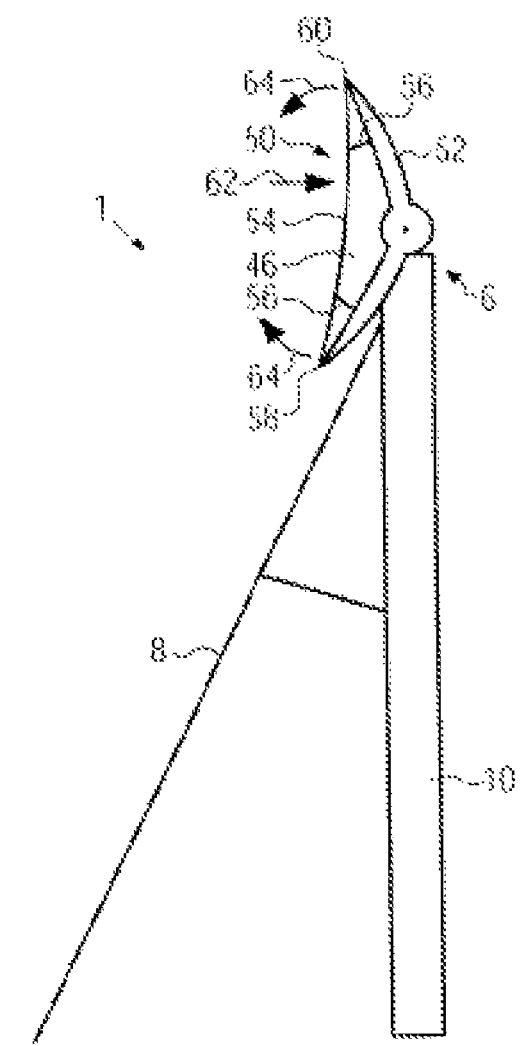
FIG. 8 depicts a schematic representations of various embodiments of a distal end of the manipulator tool according to the invention.

FIG. 8 shows a variant of FIG. 7, in which a modification 50 of the manipulator tool 1 is employed as a tool 46 which is passively deflected, in contrast to the manipulator tool 1.

The modification 50 also comprises an at least flexurally stiff cheek 52 and an at least tension-proof cheek 54 which are connected with each other via at least one hinge element 56.

The modification 50 is hinged to the tool holder 44 in the central region of the at least flexurally stiff cheek 52, so that the at least tension-proof cheek 54 extends between the two ends of the at least flexurally stiff cheek 52 which are spanned like an arch.

If an object, which is not shown in FIG. 8, exerts a compressive force 62 onto the at least tension-proof cheek 54 of the tool 46, the at least tension-proof cheek 54 yields at this point. The unloaded ends simultaneously move in a movement 64 towards the point of application of the compressive force 62 and try to grip around the object that exerts a force. In this manner, the modification 50 automatically adapts to an object.

Figure 9:
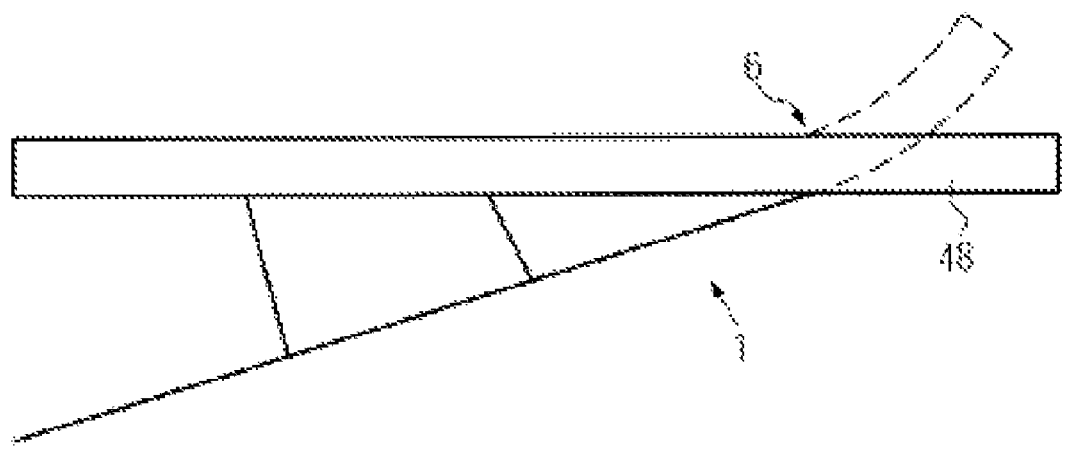
FIG. 9 depicts a schematic representations of various embodiments of a distal end of the manipulator tool according to the invention.
Figure 10:
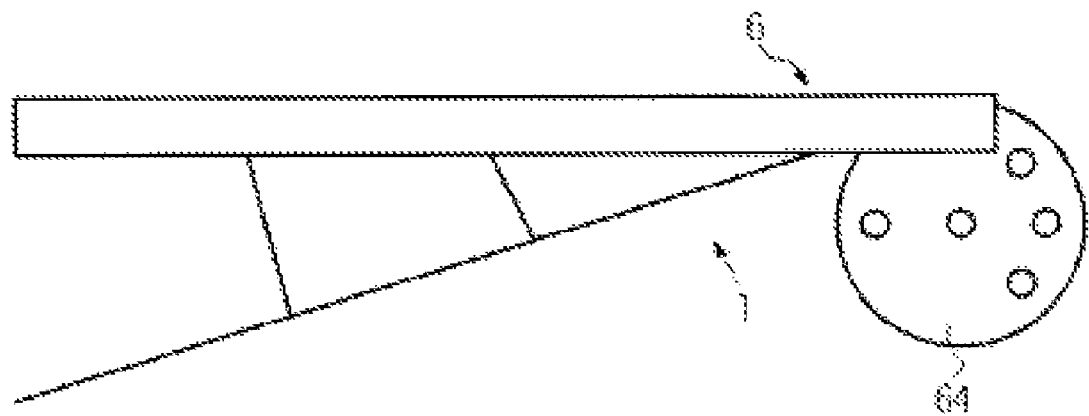
FIG. 10 depicts a schematic representations of various embodiments of a distal end of the manipulator tool according to the invention.

In the embodiment of FIG. 9, the extension 48 is embodied to be elastically yielding and can be used, for example, for receiving cleaning and/or scratching tools. In FIG. 10, a flat, for example, a disk or plate-shaped expansion 64 is provided at the manipulator tool 1, which can also be a carrier for scratch and/or cleaning tools.

Figure 11:
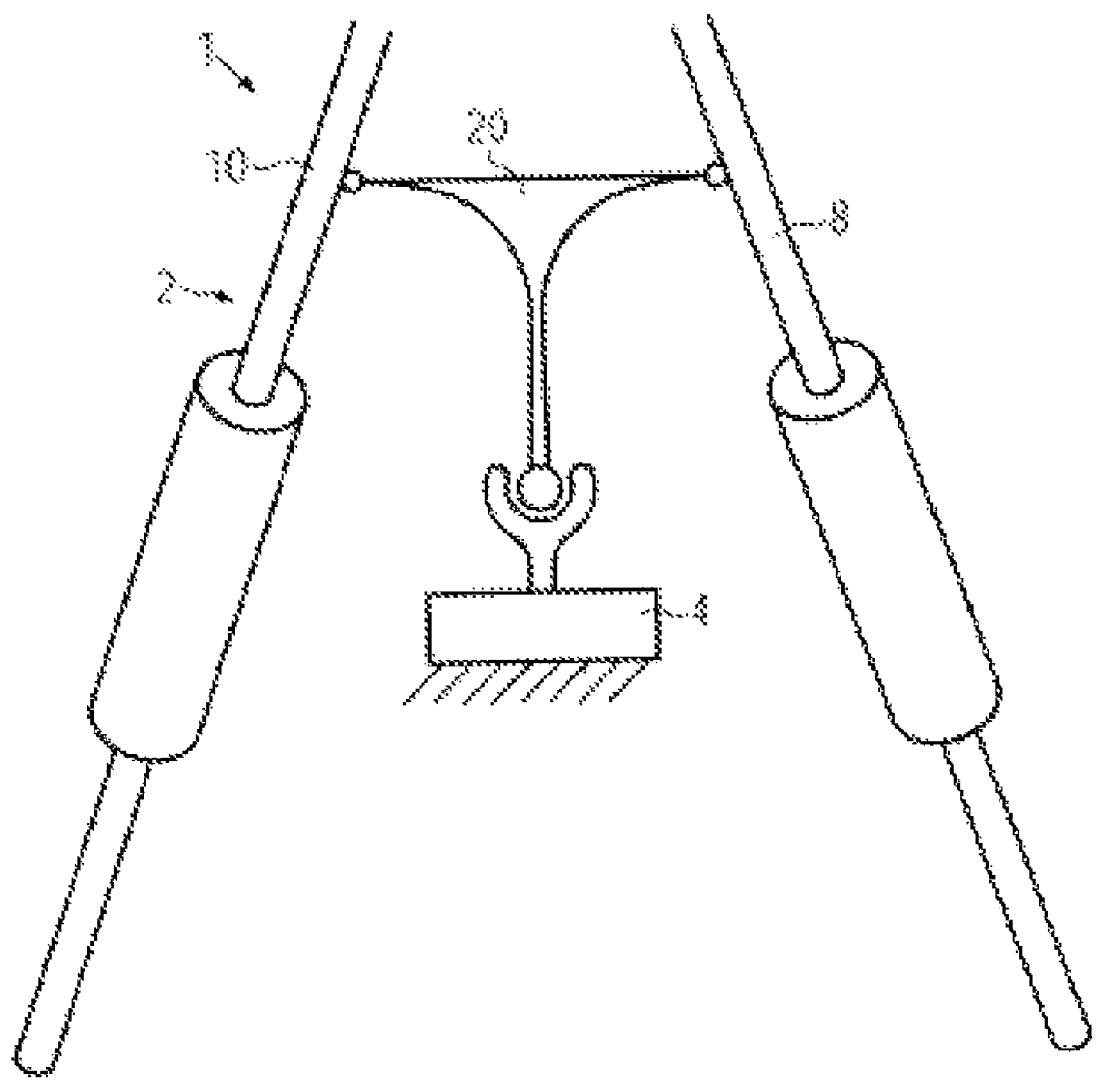
FIG. 11 depicts a schematic representation of an embodiment of a hinge element of the manipulator tool according to the invention.

FIG. 11 shows a further embodiment of the tool carrier 4 in which only the proximal end 2 is shown. In the embodiment of FIG. 11, the manipulator tool 1 is fixed to the tool base 4 via a hinge element 20. This embodiment is in particular suited for the embodiment of FIGS. 5 and 6, where both cheeks 8, 10 can be driven lengthwise. The fixing of the hinge element 20 can be accomplished without moments, depending on the desired deformation geometry and loading situation in the application, as represented in FIG. 11; however, the hinge element 20 can also be firmly clamped at the tool base 4.

Figure 12:
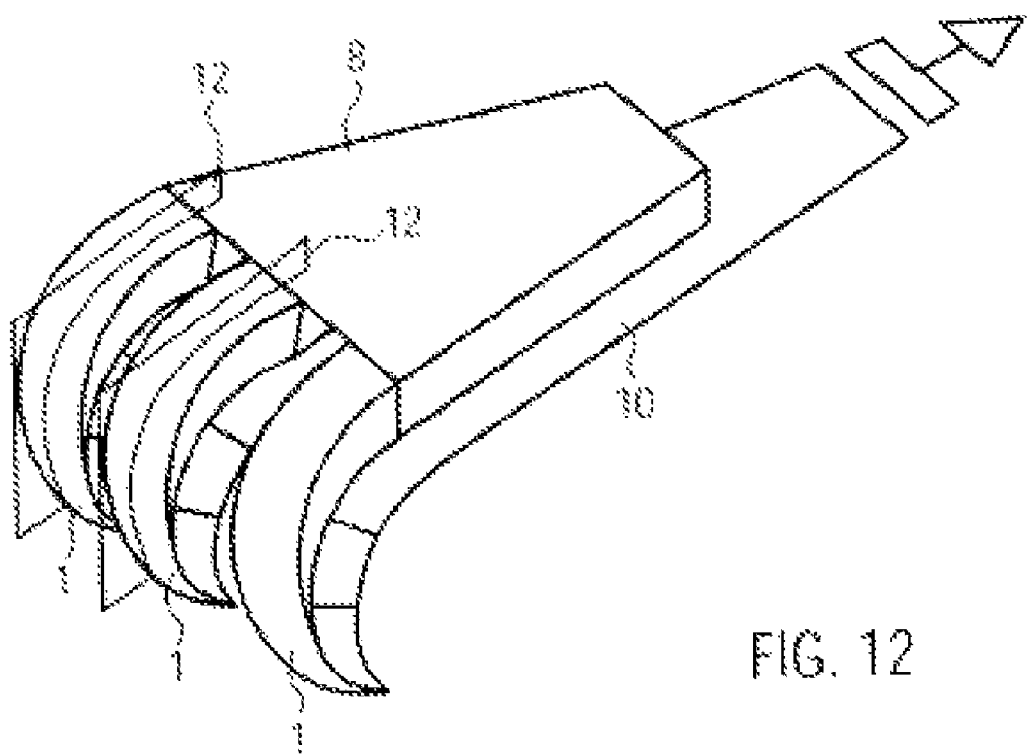
FIG. 12 depicts a schematic representation of a further embodiment of the manipulator tool according to the invention.

As is shown in the embodiment of FIG. 12, several manipulator tools 1 can also be arranged one next to the other and actuated independently or simultaneously. The manipulator planes 12 can extend in parallel or intersect. For example, the two cheeks 8 and 10 can fan out like fingers, or the individual fingers can be formed by one manipulator tool 1 each. In the region of the carpus, the stiff cheek can, if desired, have a high resistance to bending or be configured to have a high stiffness to reduce or prevent any deformation in this region and to restrict the deformation essentially to the region of the fingers.

Thus, the manipulator tool 1 can also be employed as gripping tool.

Figure 13:
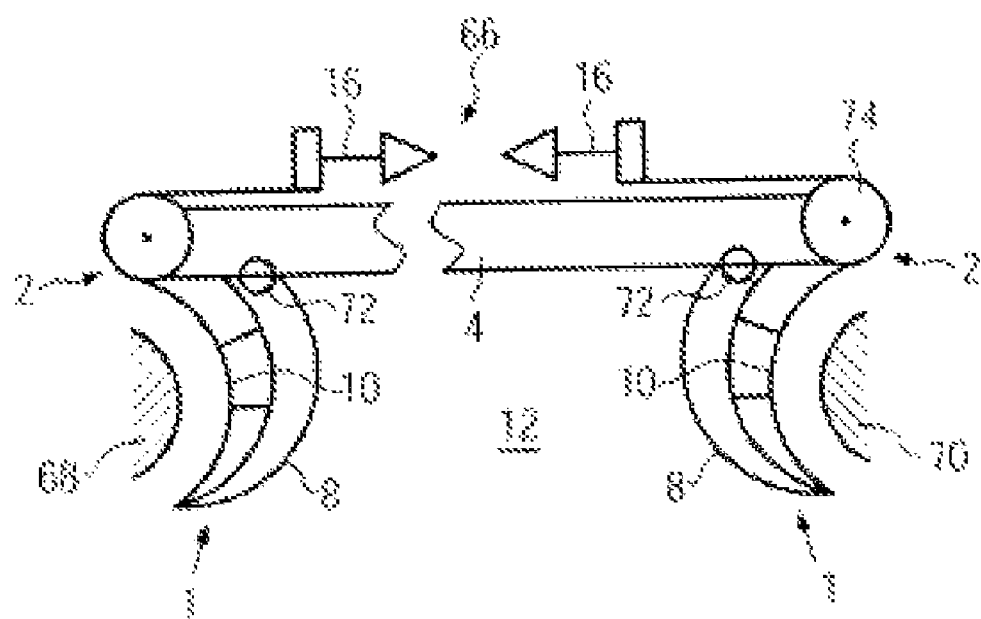
FIG. 13 depicts a schematic representation of an embodiment of a holding and/or expanding tool according to the invention.

FIG. 13 shows a further embodiment in which two manipulator tools 1 are arranged in parallel to each other, where the proximal ends 2 are arranged at a common tool base 4 and the at least flexurally stiff cheeks are assigned to each other. Manipulator tools 1 are located in at least nearly the same manipulator plane 12, in FIG. 13 the plane of projection.

An expanding and/or gripping tool 66 results from the arrangement according to FIG. 13, which can be expanded between two objects 68 and 70 or in an opening of an object. For this, the manipulator tools 1, which are preferably straight or bent with respect to each other in their rest position, are inserted between the objects 68 and 70, and subsequently the cheeks 10 are driven to move lengthwise by a pulling force 16 acting on each cheek 10. Thereupon, the cheeks 8 bend in the direction towards the objects 68 and 70, and the holding and/or expanding tool wedges between the objects 68 and 70.

The two manipulator tools 1 can be arranged to be movable towards each other or away from each other along the tool base 4, so that the distance between the two manipulator tools 1 can be changed. In addition, the first cheek 8 can be fixed to the tool base 4 via a joint 72, so that, when the pulling force 16 is applied, first the cheek moves against the respective object 68 and 70 assigned to it essentially without any deformation and only bends when the pulling force is continued to be applied while the cheek lies around the object 68 and 70. The cheek 10 or a traction means connected to it can be deflected via a deflection roller 74.

Of course, the joint 72 and the deflection roller 74 can be also used in any other embodiment described herein.

Figures 14, 15:
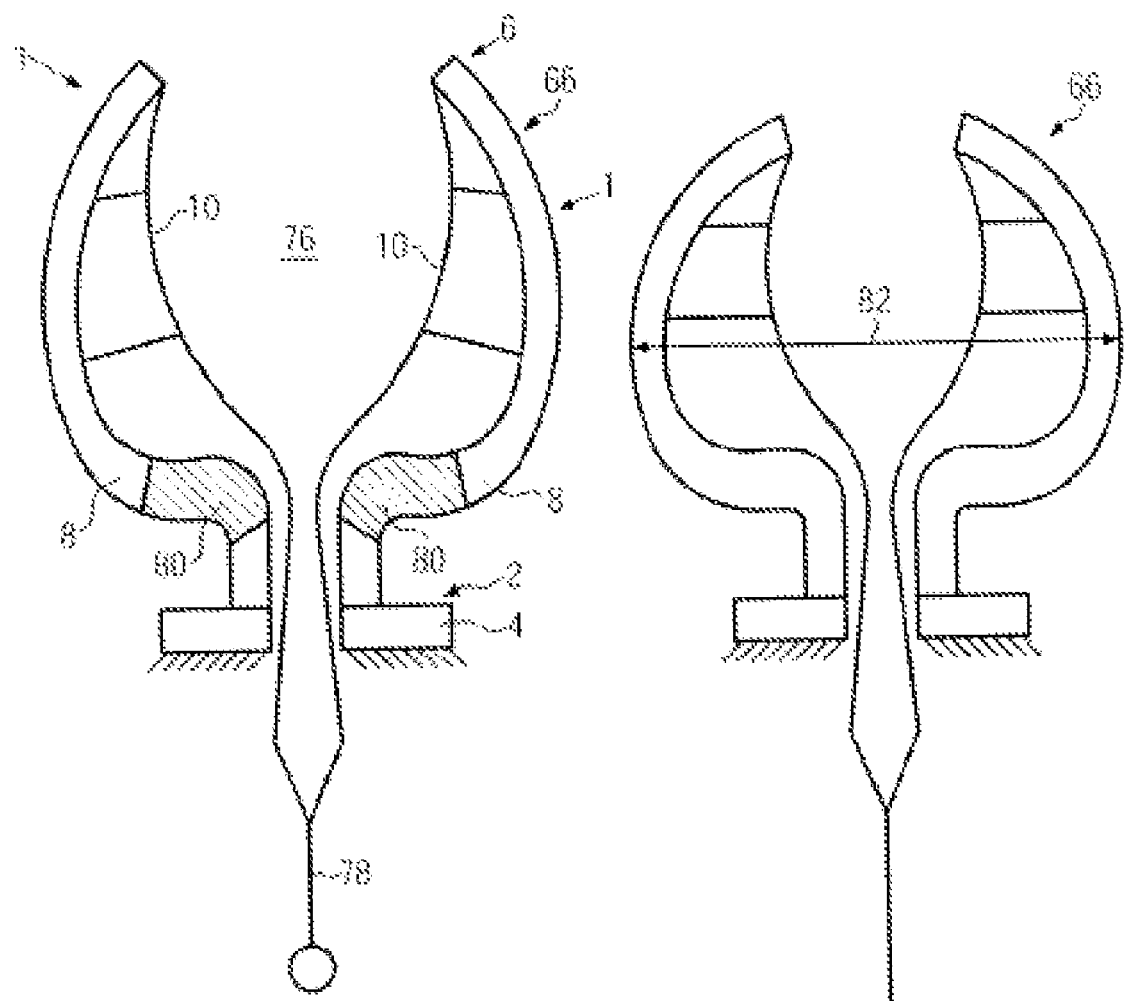
FIG. 14 depicts a schematic representation of a further embodiment of a holding and/or expanding tool according to the invention in an original position.
FIG. 15 depicts a schematic representation of the embodiment of FIG. 14 in a deformed position.

FIGS. 14 and 15 show a further embodiment of a holding and/or expanding tool which is formed of two manipulator tools 1 which are opposed with respect to a space 76, which, for example, is used for receiving a workpiece. In the embodiment of FIG. 14, the second cheeks 10 face each other and delimit the space 76. The space 76 is open towards the distal end 6, so that a workpiece (not shown) can be inserted from this side.

The two first cheeks 8 are fixed to the tool base 4 at the proximal end 2. The second cheeks 10 are brought together at the proximal end 2 and end in a common traction means 78, so that they are simultaneously actuated if they are pulled.

The distribution of the stiffness of the first cheeks 8 in the direction from the proximal end 2 to the distal end 6 is selected such that in the region of the proximal end of the space 76, a region 80 of reduced stiffness is formed. This leads to the region 80 deforming to a greater extent than the other region of the first cheek 8 if a pulling force 16 is applied (FIG. 15) to the second cheeks 10. The region 80 thus serves as elastic joint about which distal ends 6 of the two manipulator tools 1 swivel.

The region 80 of reduced stiffness, as it is shown in FIG. 14, can be accomplished by a shaping process in which stress concentrations are formed in the material. As an alternative or in addition, this function can be achieved by a reduced wall thickness or by using a material of a lower stiffness. The region 80 can be used instead of a joint 72 if an elastic resetting function is important.

The described holding and/or gripping function of the embodiment of FIG. 14 can be, as by the way also in the other embodiments, easily reversed to an expanding function if the first cheeks 8 assume the position shown in FIG. 14 in the non-deformed state. Then, the first cheeks 8 are elastically deflected towards each other by the pulling force 16, and the width 82 of the holding and/or expanding tool is reduced, so that it can be inserted into an opening. If the pulling force is reduced, the first cheeks 8 try to expand again elastically.

Figure 16:
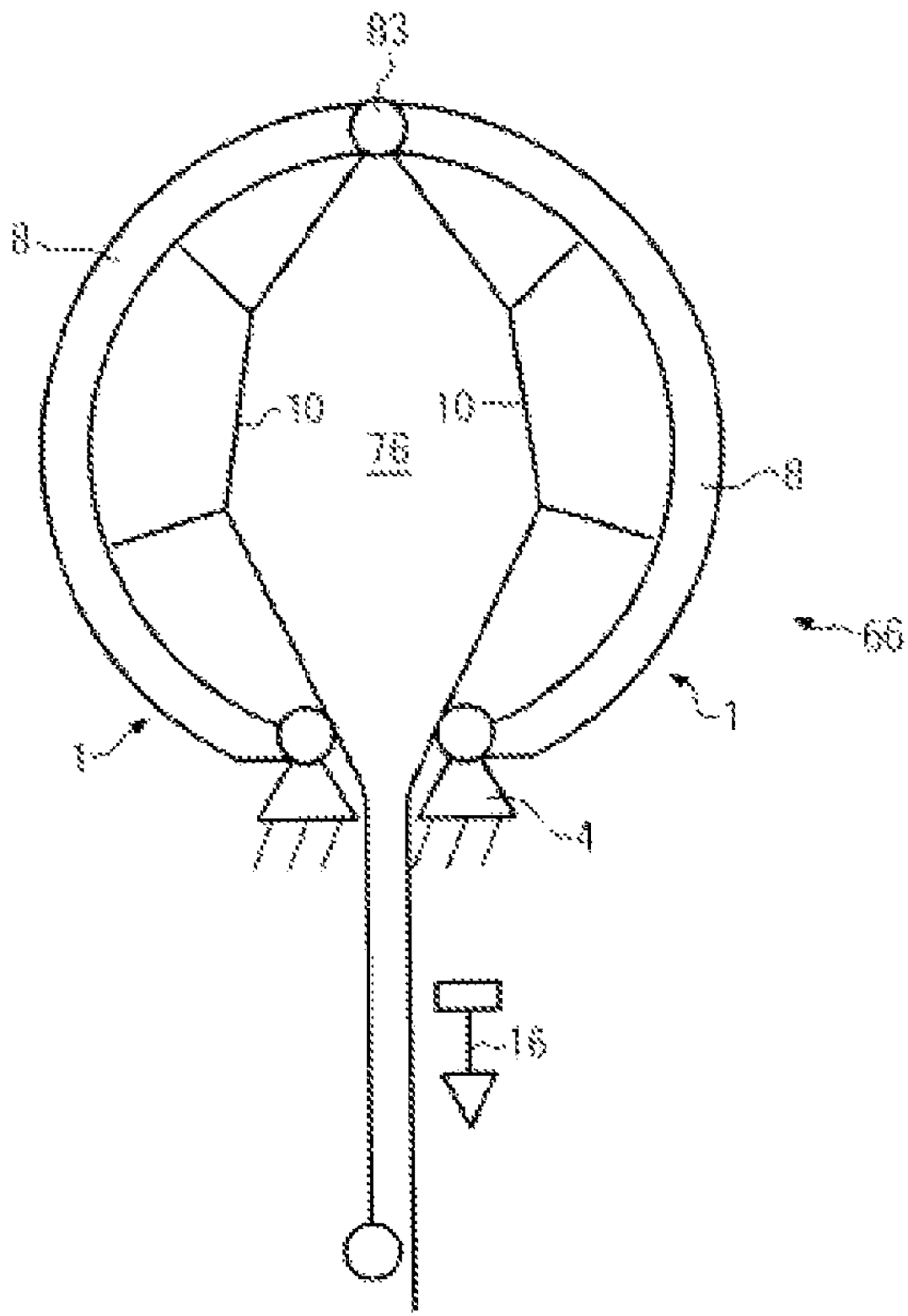
FIG. 16 depicts a schematic representation of a further embodiment of a holding and/or expanding tool according to the invention.

The embodiment of FIG. 16 differs from the embodiment of FIGS. 14 and 15 by a hinge joint of the distal ends 6 of the two manipulator tools 1, so that an annularly closed interior 76 is formed. This embodiment is suited in its basic form for expanding, but also for securely holding tubular objects.

Figures 17, 18:
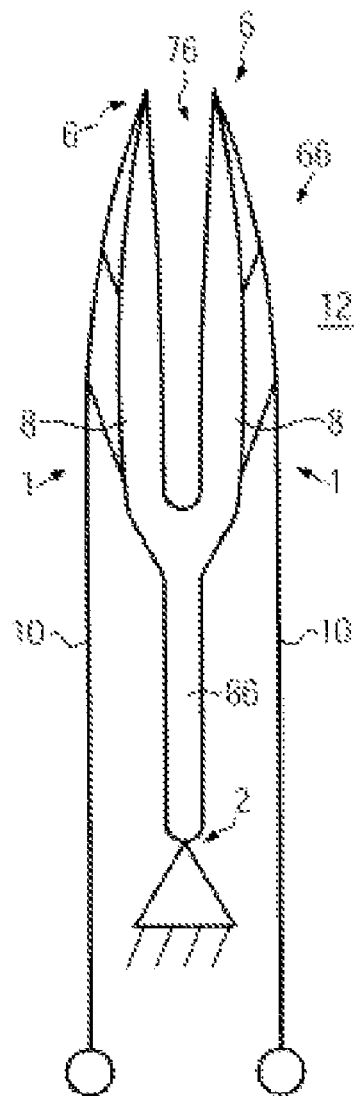
FIG. 17 depicts a schematic representation of a further embodiment of a holding and/or expanding tool according to the invention in an original position.
FIG. 18 depicts a schematic representation of the embodiment of FIG. 17 in a deformed state.

In FIGS. 17 and 18, another example of a holding and/or expanding device 66 with two manipulator tools 1 is shown. This tool, too, can be optionally employed as expanding and/or holding tool, depending on the pre-bending of the first cheeks 8.

In the embodiment of FIGS. 17 and 18, the two first cheeks 8 are connected to each other at a root 84, which optionally can also be embodied as joint 72. The root 84 continues in a stem 86, which is connected to the tool base 4 at the proximal end 2. The two at least tension-proof cheeks 10 face away from each other and are each independently movable lengthwise. In the rest position, which is shown in FIG. 17, the two first cheeks 8 extend nearly in parallel with respect to each other in the manipulator plane 12 and form the space 76 between them. If a pulling force is applied to the second cheeks 10, the first cheeks 8 move away from each other, increasing the space 76. In this embodiment, the holding and/or expanding tool is in particular suited, for example, for putting up or expanding workpieces like an umbrella between the distal ends 6 of the two manipulator tools 1 opposed to each other with respect to the space 76.

Figure 19:
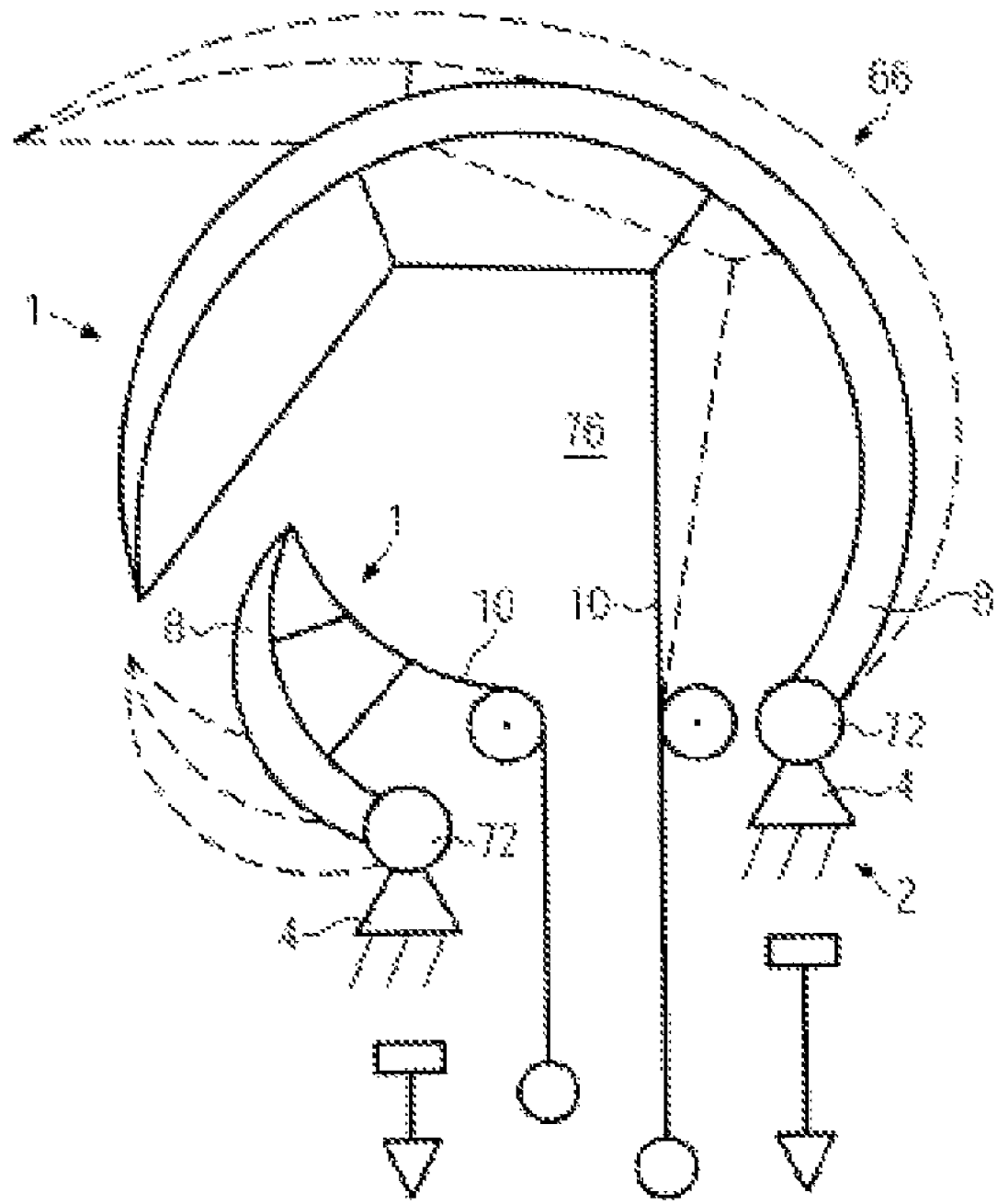
FIG. 19 depicts a schematic representation of a further embodiment of a schematic holding and/or expanding tool.

Finally, with the holding and/or expanding tool, claw-like structures can also be created, as is shown in FIG. 19. Two manipulator tools 1 delimit a space 76 with their second cheeks 10. The second cheeks 10 can be connected to the tool base 4 at the proximal end 2 of the holding and/or expanding tool 66 by means of joints 72. The one manipulator tool 1 is clearly smaller than the other manipulator tool 1 and closes the space 76 in the deformed state represented in continuous lines, while the larger manipulator tool 1 externally lies against the first cheek 8 of the smaller tool with its second cheek 10.

Figure 20:
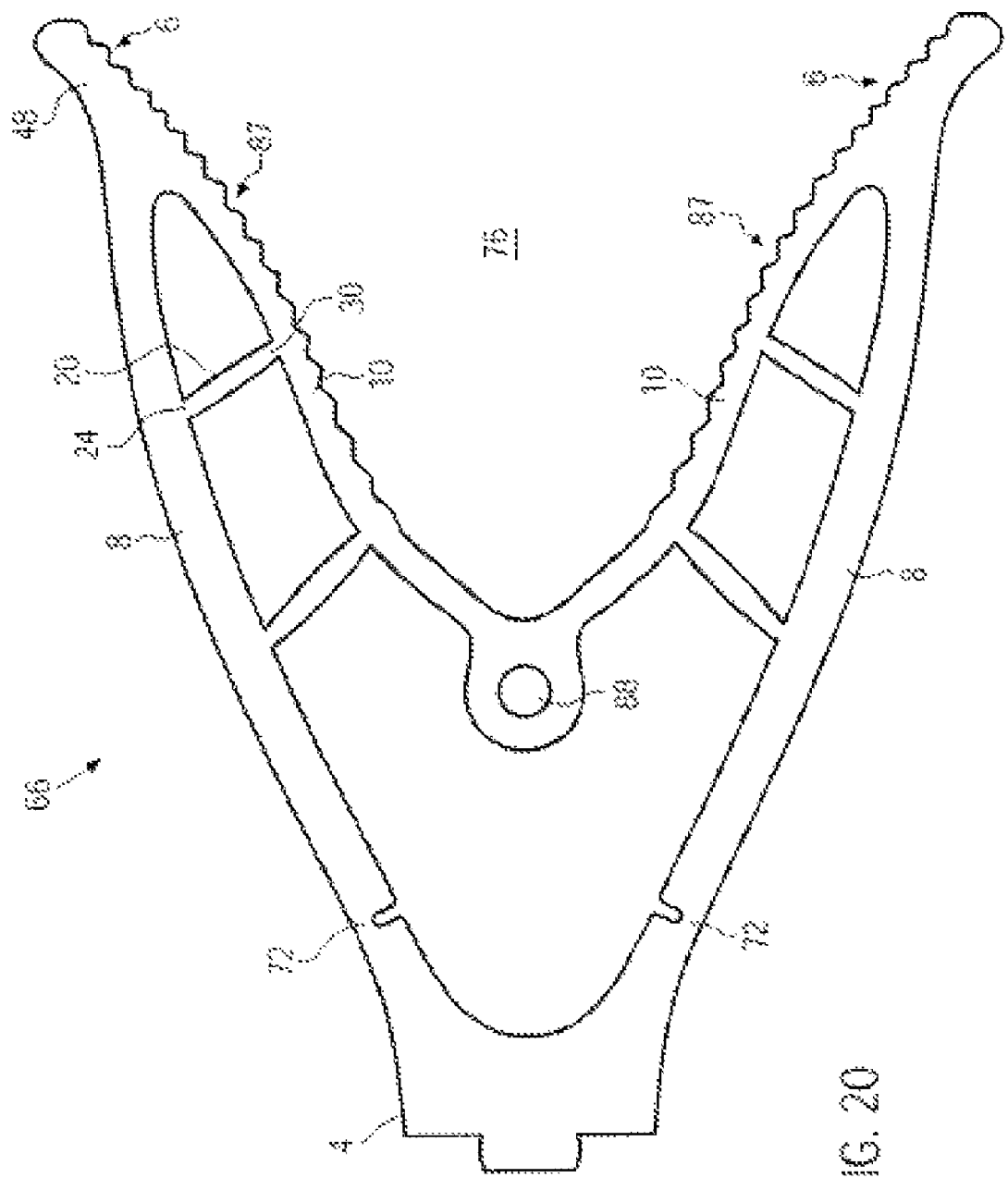
FIG. 20 depicts a schematic representation of a further embodiment of a holding and/or expanding tool according to the invention.

With reference to FIG. 20, an embodiment of a holding and/or expanding tool 66 formed in one piece is shown, which can be manufactured of a plate material by means of an injection molding, punching or cutting method.

Both cheeks 8 and 10 of the manipulator tools 1 forming the two jaws 87 are stiff, where the second cheeks 10 facing the space 76 have a smaller wall thickness than the first cheeks 8. The small wall thickness also results in a higher flexibility of the second cheeks 10, so that they more easily lie around objects to be gripped.

As by the way also in the other embodiments, the surface of the cheeks performing the holding and/or expanding function which faces the objects to be handled can be structured as required. For example, in the embodiment of FIG. 20, the second cheeks 10 comprise a ribbing transverse to the longitudinal direction.

The connection permitting a shearing movement via the at least one hinge element 20 is achieved in the embodiment of FIG. 20 by the design in the region of the mounting points 24 and 30. Due to the nearly right-angled connection of the elements 20 to the cheeks 8 and 10 and the wall thickness that is slightly reduced in the region of the mounting points 24 and 30, movability is increased in the region of the mounting points 24 and 30, so that a joint or articulating function is achieved at these points.

The outer of first cheeks 8 are connected to the tool base 4 via a joint 72, which is created by an area of weakness in the form of a recess.

At the distal end 6, the cheeks 8 and 10 are again connected to each other, forming an extension 48. The extension 48 permits a soft gripping of objects. At their proximal ends, the second cheeks 10 are connected with each other in one piece. At the point of connection of the two second cheeks 10, a coupling element 88, for example in the form of an eye, can be provided.

The tool 66 shown in FIG. 20 can be inserted at the end of a manipulator tool 1, as it is shown in FIGS. 1 to 6. If the tool base and the coupling 88 are exchanged in the embodiment of FIG. 20, or if compressive forces are introduced at the coupling 88, an expanding tool is formed. For this, it would make sense to provide the ribbing not at the cheeks 10, but at the cheeks 8.

Figures 21, 22:
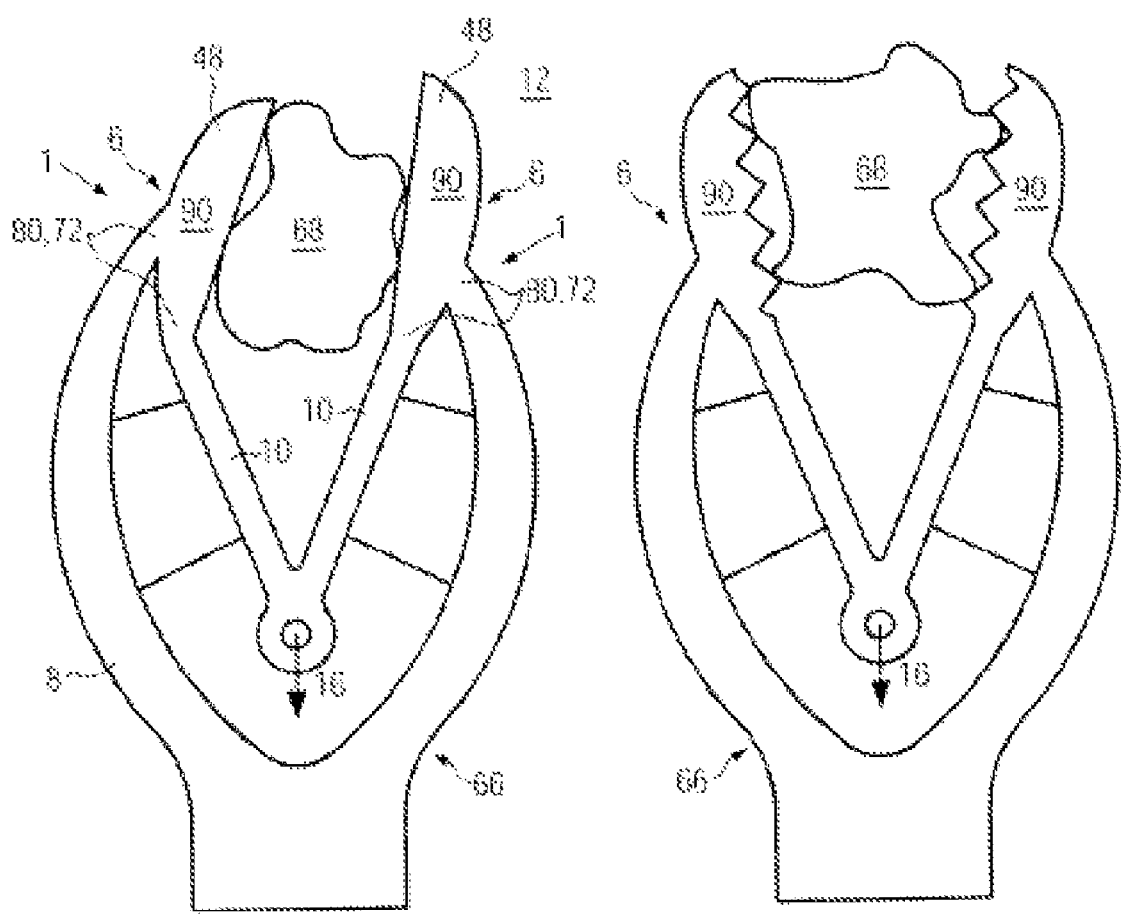
FIG. 21 depicts a schematic representation of a modification of the holding and/or expanding tool of FIG. 20.
FIG. 22 depicts a schematic representation of FIG. 20.

FIG. 21 shows how an object 68 can be gripped in a shape-adapting manner by the combination of two manipulator tools 1 according to the invention to form a holding and/or expanding tool 66. The cheeks 10 grip the object 68 as a result of the pulling force 16 and adapt to its outer contour in the manipulator plane 12. The adaptation to the contour of the object 68 also transmits to an extension 48, which is configured integrally at the distal end at the inner surface of the cheeks 10 together with a reinforced gripping region 90. The adaptation to the shape can be accomplished by the hinged connection of the gripping region 90 via joints 72 or regions 80 of reduced flexural stiffness with the outer cheek 8 and the rest of the cheek 10.

FIG. 22 shows how the gripping region 90 can adapt to the contour of another object 68 due to the hinged connection.

Figure 24:
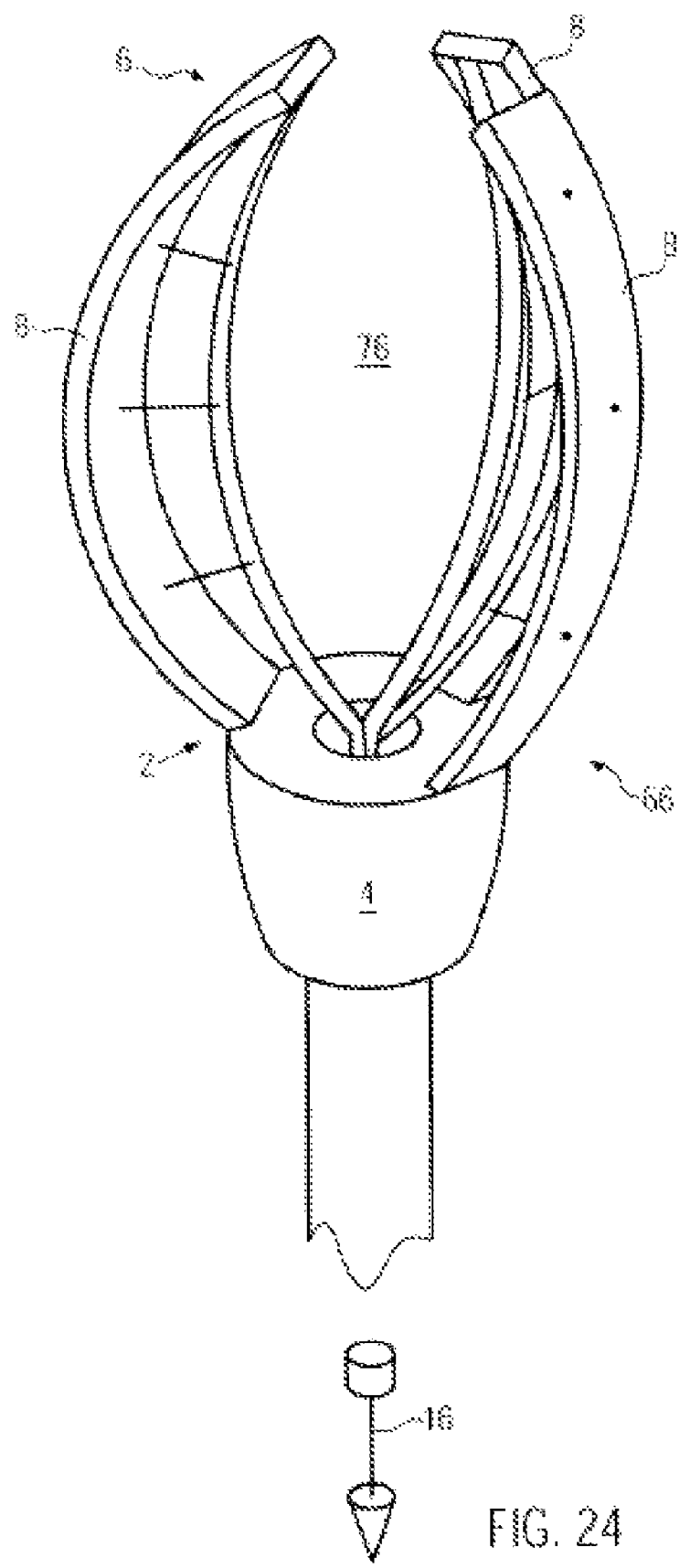
FIG. 24 depicts a schematic representation of the embodiment of FIG. 23 in a deflected position.

An embodiment of the holding and/or expanding tool 66, which is particularly suited for endoscopic applications is schematically shown in FIGS. 23 and 24. In FIG. 23, the holding and/or expanding tool is closed, in FIG. 24 it is represented in a gripping position without gripped object.

The holding and/or expanding tool 66 comprises three or more manipulator tools 1, which surround an interior 76 in a star-like configuration and which are attached within an essentially circular outer contour. In this embodiment, the holding and/or expanding tool 66 can be used, for example, in connection with endoscopes and shifted through them.

At the outer side of the holding and/or expanding tool 66, the at least flexurally stiff or first cheeks 8 are arranged to be firmly clamped at the tool base 4. Clamping is here accomplished via elastically pretensioned joints which generate a spring force moving the cheeks 8 away from each other. The at least tension-proof or second cheeks 10 face the space 76. A pulling force 16 can be applied to the at least tension-proof cheeks 10 through a central opening 92 in the tool base 4 that preferably does not project over the outer contour of the manipulator tool 1.

If no object is arranged in the space 76, a pulling force 16 causes the manipulator tools 1 to move against the spring force of the elastically pretensioned joints towards each other essentially without deformation and to be able to assume the position represented in FIG. 23 and also to be totally closed in the form of a bud. However, this necessitates that the stiffness in the joint is smaller than the stiffness of the stiff cheeks. In the closed position, the embodiment of FIGS. 23 and 24 has a narrow cross-sectional shape, so that the gripping tool can be in particular employed in constricted space situations, for example as fruit picker between branches, or it can be passed through between organs at the end of an endoscope.

If an object is located in the space 76 in the opened state, first the manipulator tools 1 are swiveled inwards without deformation until they contact the object when a pulling force is applied. Only the further longitudinal movement of the at least tension-proof cheeks 10 causes the deformation of the manipulator tools or stiff cheeks 8 shown in FIG. 2, which in the process fit to the outer contour of the object.

Figure 25:
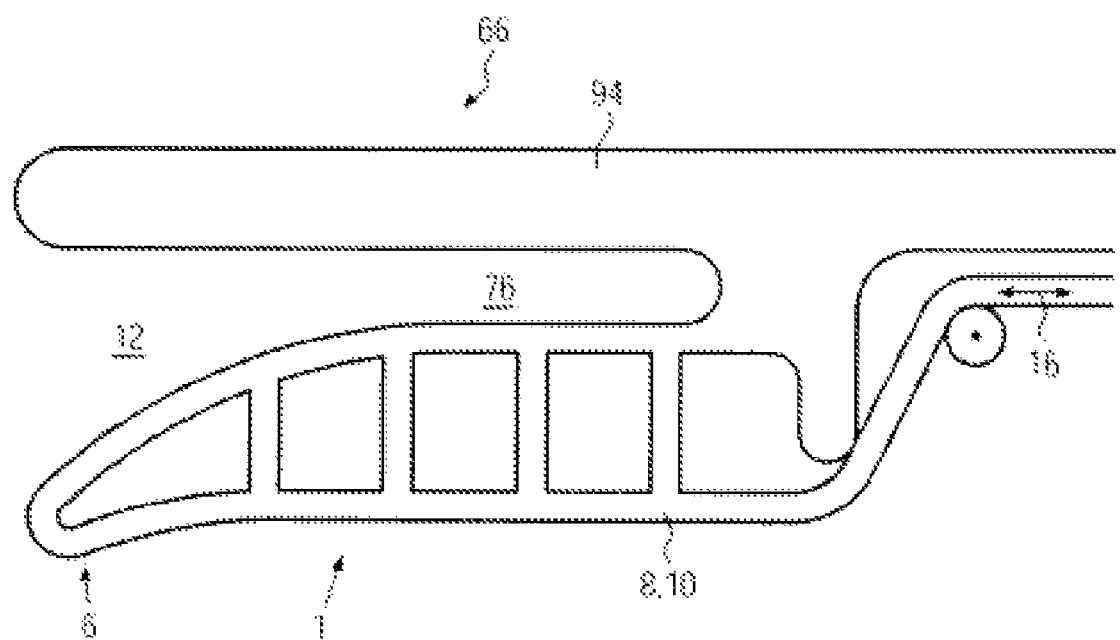
FIG. 25 depicts a schematic representation of a further embodiment of a holding and/or expanding tool according to the invention.

Thus, according to the embodiment of FIG. 25, the manipulator tool 1 can have an original position in which it presses against the jaw 94. By pulling at the outer cheek 10, it assumes the position shown in FIG. 25 in which it is moved away from the opposite jaw 94, so that an object can be inserted into the space 76.

The embodiment of the jaw 94 can be effected depending on the desired function. In a suited gripping function, the jaw 94 can form a contact surface for an object to be held in the space 76. However, the jaw 94 can also be embodied as blade to cut in two the object arranged in the space 76 when the pulling force 16 decreases. This is in particular useful in the field of vascular surgery if the holding and/or expanding tool represented in FIG. 25 is employed, for example, in endoscopes.

The embodiment of FIG. 25 can also be employed as handle which permits to operate further non-depicted tools via the force 16 if the jaw 94 and the manipulator tool 1 have a correspondingly ergonomic design.

Figure 26:
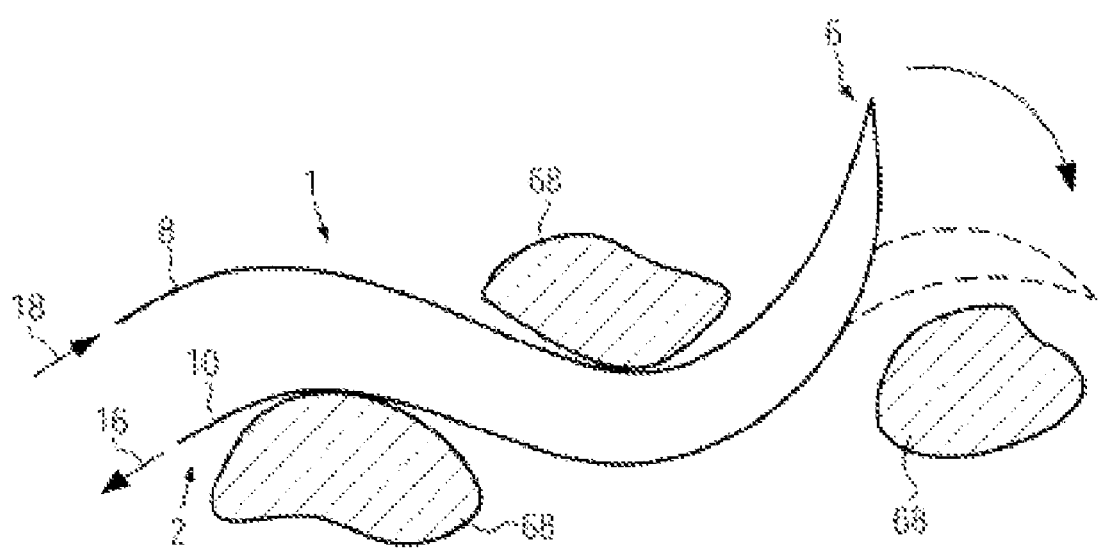
FIG. 26 depicts a schematic representation of a manipulator tool for endoscopy-like applications endoscopy.

FIG. 26 shows a manipulator tool 1 which is employed as endoscope and threaded through between objects 68. The basic structure of such an endoscope can correspond to the construction of the embodiment of FIGS. 5 and 6, in which the two cheeks 8, 10 are stiff and take up pulling as well as compressive forces, or else the one cheek 8 only takes up compressive forces and the other cheek 10 only takes up pulling forces. As long as the distal end 6 of the manipulator tool 1 is free, the tip can be moved and placed around the objects 68 by applying the forces 16, 18. In this manner, the distal end 6 can always be oriented such that it points between two adjacent objects 68, and the manipulator tool 1 can be inserted in-between. In the final position, a tool attached to the distal end 6 or an observation apparatus can be brought into position again around a last object 68, or this last object can be gripped, as is indicated by the dashed line in FIG. 26.

For a better overview, the hinge elements 20 are omitted in FIG. 26.

Figure 27:
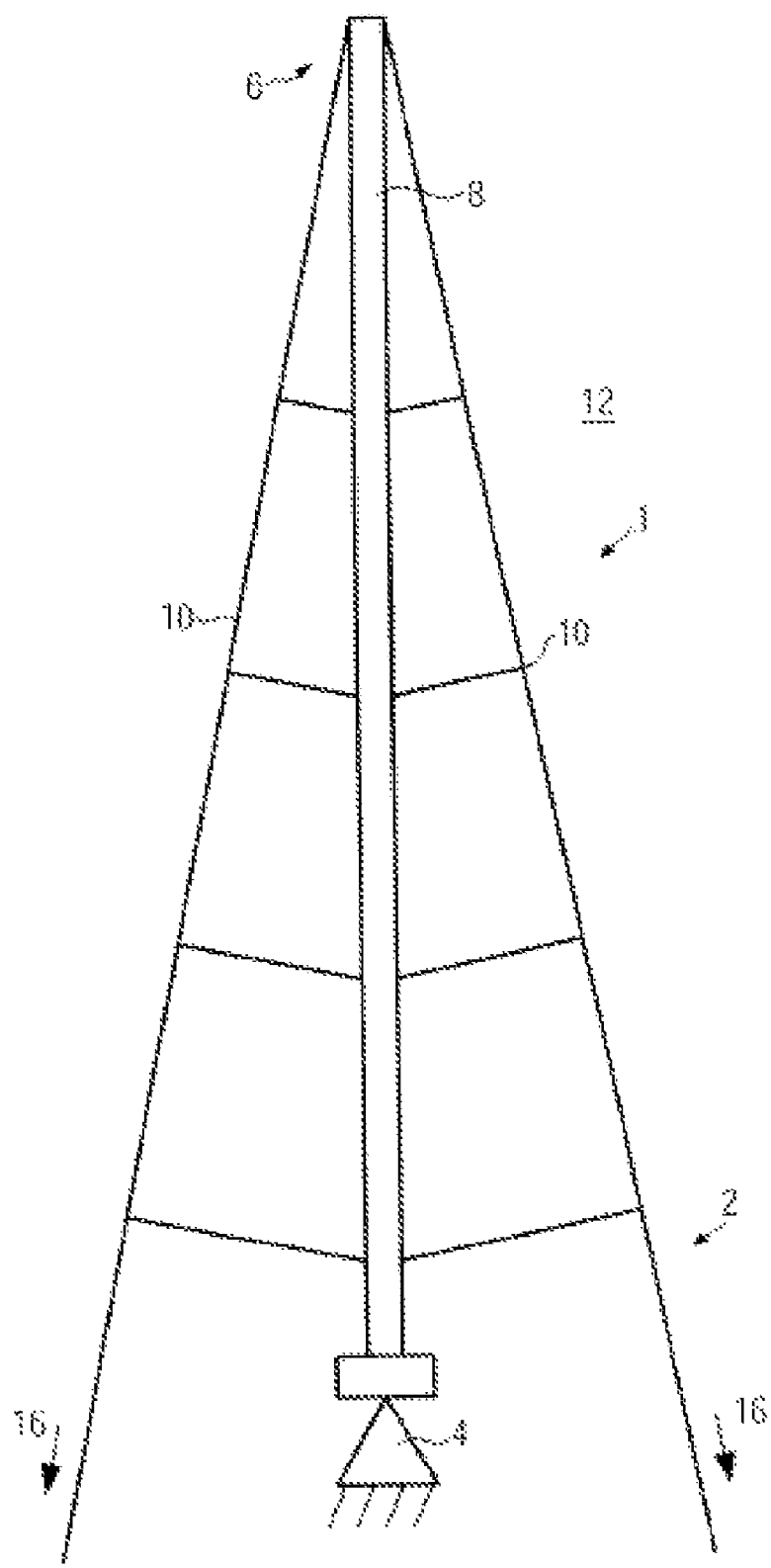
FIG. 27 depicts a schematic representation of a further embodiment of a manipulator tool according to the invention, also in particular for endoscopy-like applications.

The function described in FIG. 26 can also be achieved by the embodiment of the manipulator tool 1 shown in FIG. 27, where a central stiff cheek 8 is shared by at least two, at least tension-proof cheeks 10. The central stiff cheek 8 is held at the tool base 4, preferably so as to swivel. Each individual cheek 10 can be driven lengthwise at its proximal end 2. By pulling at one of the cheeks 10, a bend of the stiff cheek 8 into the respective desired direction can be achieved. Here, the cheeks 10 can also be arranged in more than one manipulator plane 12 and thus cause a three-dimensional bend of the central cheek 8. This, too, is an advantage for an endoscopic application.

As in the embodiment of FIG. 27 pairs of driven cheeks 10 acting in opposite directions are provided each, the at least flexurally stiff cheek 8 does not have to be embodied as spring element, as the readjustment can be effected by pulling at the opposite cheek 10, respectively.

Another embodiment that permits a three-dimensional bend of the manipulator tool 1 is shown in FIGS. 28 to 30. Here, too, at least three, but preferably four cheeks 8 and 10 are provided distributed across a base 96 of the tool base 4 in the circumferential direction 98, the cheeks being connected by hinge elements 20 in the circumferential direction that means transverse to their longitudinal extension.

Via spacers 100, the cheeks 8 and 10 are connected to a flexible sleeve 102 which delimits the structure to the outside and receives the cheeks 8 and 10, the hinge elements 20 as well as the spacers 100. The minimum required number of stiff cheeks depends on the number of cheeks present altogether in the manipulator tool 1 and on the number of stiff cheeks required for shaping and stiffness.

If the sleeve 102 is sufficiently stiff, so that it supports the cheeks 8 and 10, these can also be segmented, i.e. structured by joints 104.

The spacers 100 can extend at any arbitrary location between the cheeks, hinge elements or joints and the sleeve 102. The hinge elements 20 can extend essentially in parallel to the sleeve.

If a pulling and/or compressive force 16 and 18 is introduced into the cheeks 8 and 10 in the manner already described above, this leads to a deformation of the sleeve 102, for example in the form which is shown in FIG. 29.

Figure 31:
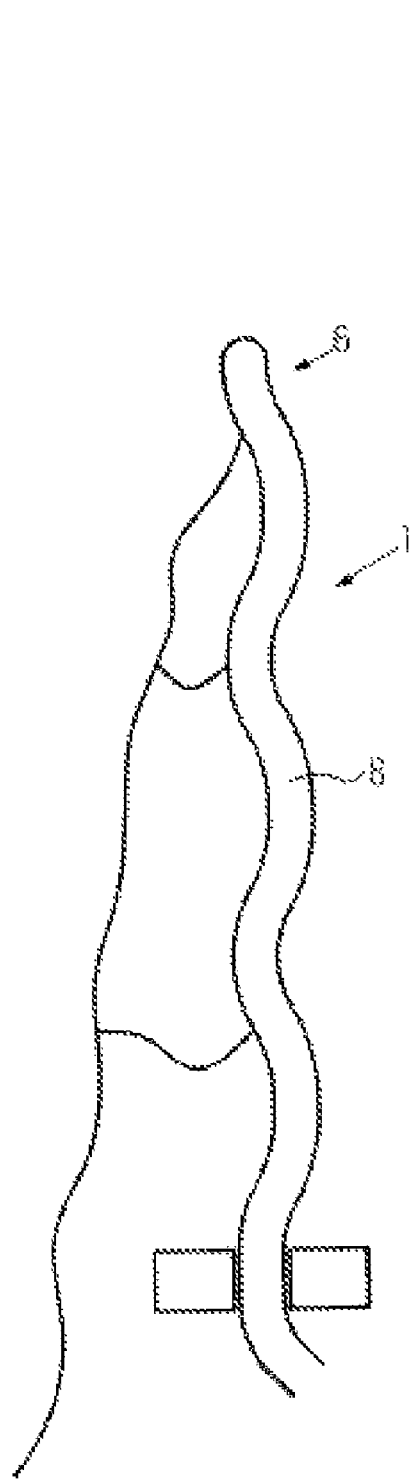
FIG. 31 depicts a schematic representation of a further embodiment of a manipulator tool according to the invention in a first operating state.
Figure 32:
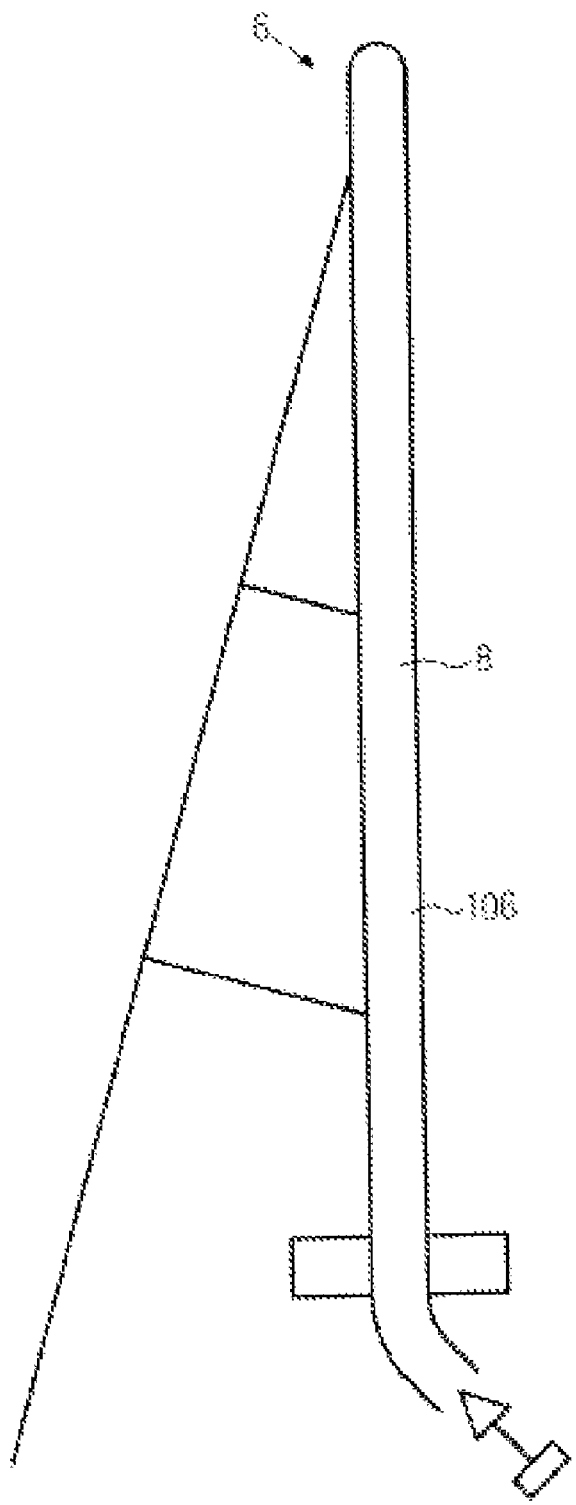
FIG. 32 depicts a schematic representation of the embodiment of FIG. 31 in a further operating state.

In the embodiment of FIG. 31, the stiff cheek 8 is hollow and flexible, so that it can be pumped up by a fluid 106 inside.

In this embodiment, the cheek 8 is limp if the fluid 106 is not under pressure or is emptied. Consequently, the manipulator tool 1 can be shifted through very small openings and subsequently be pumped up.

Figure 33:
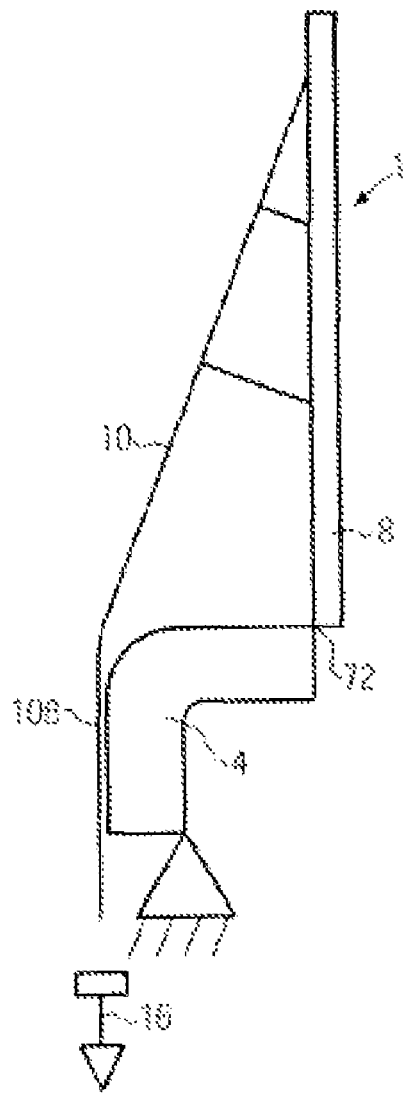
FIG. 33 depicts a schematic representations of further embodiments of manipulator tools according to the invention.
Figure 34:
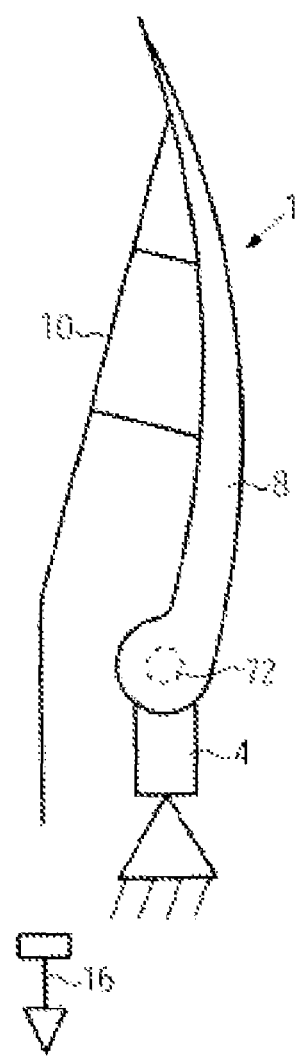
FIG. 34 depicts a schematic representations of further embodiments of manipulator tools according to the invention.
Figure 35:
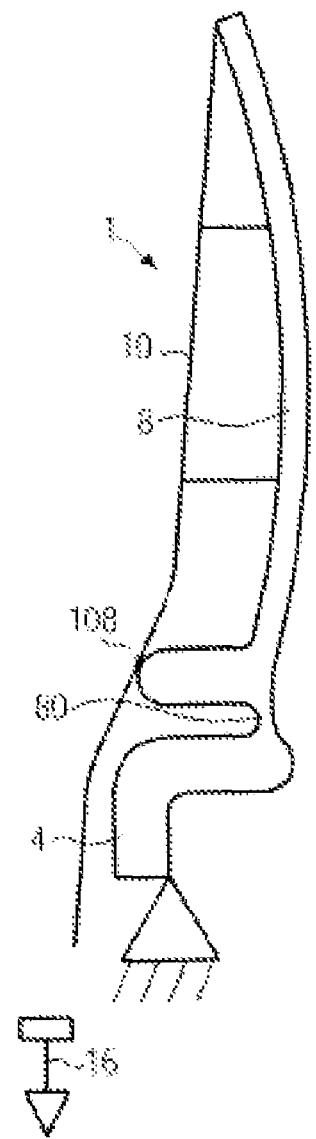
FIG. 35 depicts a schematic representations of further embodiments of manipulator tools according to the invention.

In the embodiments of FIGS. 33 to 35, on the one hand different embodiments of the connection of the at least flexurally stiff cheek 8 to the tool base 4 in the form of joints 72 in regions of reduced stiffness 80 are shown. Simultaneously, the tool base 4 can comprise an elbow 108 which serves as guide for the at least tension-proof cheek 10 on which a pulling force 16 can act.

Figure 36:
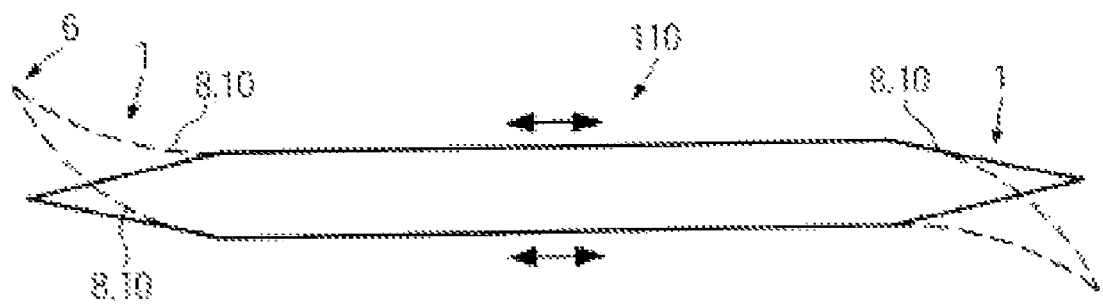
FIG. 36 depicts a schematic representation of a further embodiment of the manipulator tool according to the invention.

FIG. 36 shows an embodiment in which two manipulator tools 1 are arranged at the ends of an elongated tool 110, of which the cheeks 8 and 10 are connected to each other, so that they are always actuated simultaneously and in opposite directions.

Figure 37:
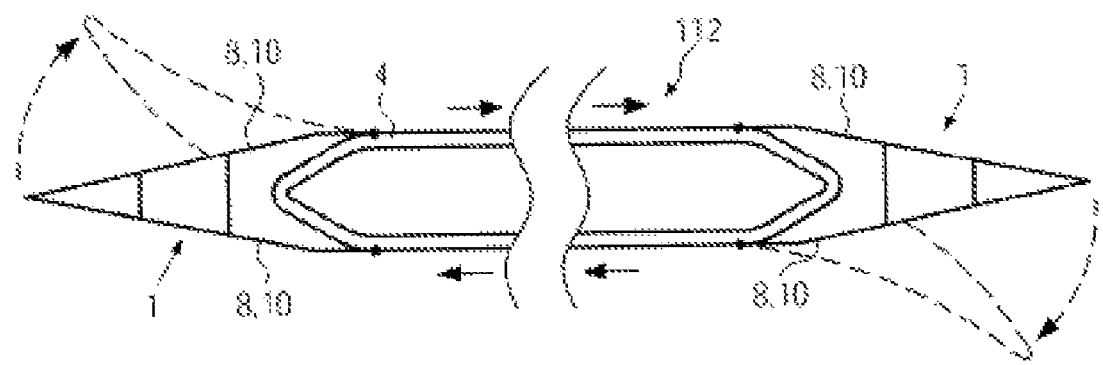
FIG. 37 depicts a schematic sectional representation through the embodiment of FIG. 36.

FIG. 37 shows, by way of example, a section through such an embodiment. The tool base 4 is formed by a for example polygonal basic body, at the two opposite ends of which the manipulator tools 1 are arranged. The region 112 between the two manipulator tools can be designed as grip. If a shear movement is applied to the tool base 4 as working movement, on one side of the tool base, a pulling force or longitudinal movement is correspondingly introduced simultaneously into the one cheek of the one manipulator tool, and a compressive force or longitudinal movement in the same direction is introduced into the cheek of the other manipulator tool. On the other side, there is a reversed direction of force. This results in a deformation of the manipulator tools 1 in the form which is shown in FIG. 37 in a dashed line.

Figure 38:
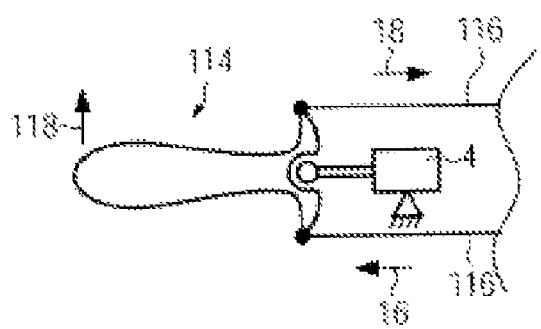
FIG. 38 depicts a schematic representation of a manual handle for actuating a manipulator tool according to the invention and/or a holding and/or expanding tool according to the invention.

FIG. 38 shows a handle 114 for simultaneously generating a compressive force 18 and a pulling force 16 in a non-depicted manipulator tool 1 which is connected with the traction/pressure means 116. The handle 14 is hinged and can be tilted, as is indicated by arrow 118. At the traction/pressure means situated in the tilting direction, a compressive force is generated, on the side facing away from the tilting direction; a pulling force 16 is generated.

The mounting of the handle 114 is preferably effected at a site stiffly connected to the tool base 4.

Figure 39:
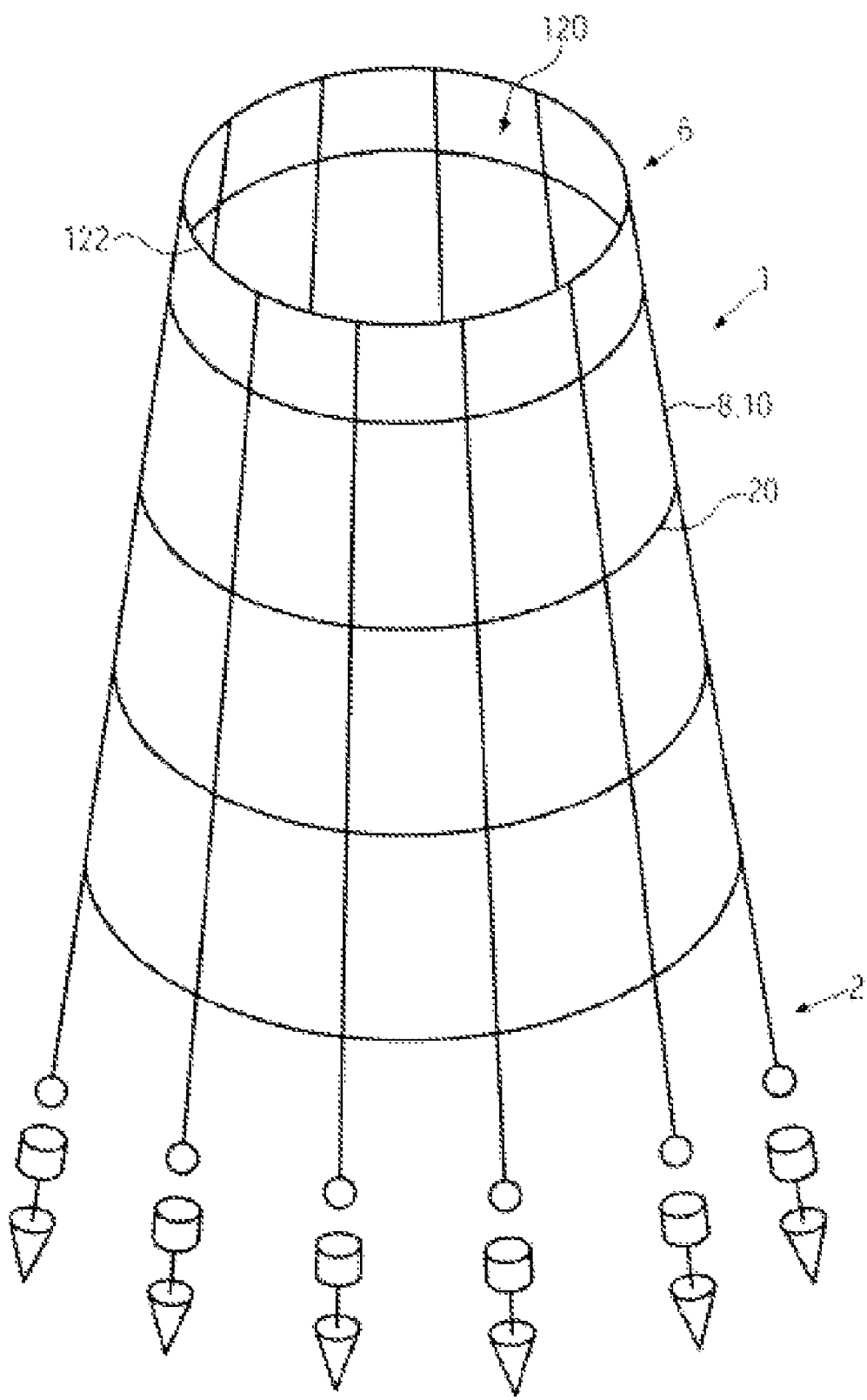
FIG. 39 depicts a schematic representation of a further embodiment of the manipulator tool according to the invention.

FIG. 39 shows the embodiment of a manipulator tool 1 in a tubular form. A plurality of cheeks 8 and 10, which can at least partially be movably longitudinally independently of each other and partially be fixed at the tool base, are annularly arranged around a center and each connected with the adjacent cheek by hinge elements 20. This arrangement results in an interior 120 which is annularly delimited by the hinge elements, and in the longitudinal direction delimited by the cheeks 8 and 10.

For the interior 120 to freely open at least at the proximal end 2 and thus to be suited for receiving further instruments or for passing through fluids, adjacent cheeks 8 and 10 are not connected at their distal end 6 in a wedge shape, but in an obtuse manner by a respective terminating element 122. The use of such an terminating element 122 is irrelevant for the effect according to the invention, as long as it is ensured in the wedge-shaped connection point 14 (FIG. 1) that the angles between the adjacent cheeks 8 and 10, which are connected to each other at this point, do not change or only change insignificantly in the deformation.

Instead of the actuation of individual lengthwise movable cheeks, the movable cheeks of a further development can be connected at the proximal end by an inherently stiff ring, via the movement of which, in particular tilting, the deformation of the tube is effected by the cheeks fixed thereto being simultaneously shifted. In this embodiment, the tube can be used as separate instrument, for example as movable tubus.

Figure 40:
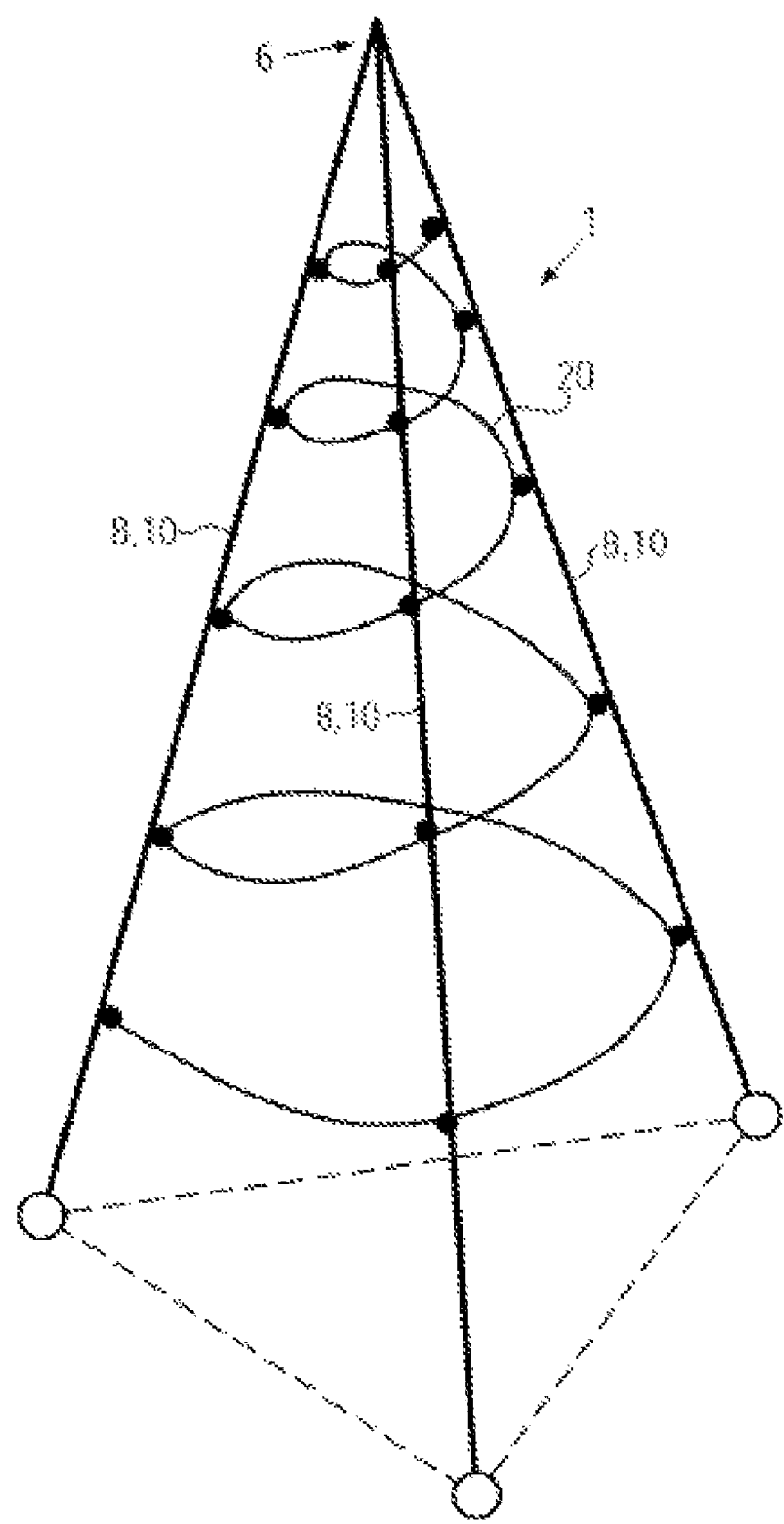
FIG. 40 depicts a schematic representation of a further embodiment of the manipulator tool according to the invention.

The form of the hinge elements 20 is mainly determined by the application case of the manipulator tool 1, as long as they fulfill their function described with reference to FIG. 2. For example, a continuous hinge element can extend helically between several cheeks 8 and 10, as is shown in FIG. 40. Instead of a helix, circles as in FIG. 39 or other geometric embodiments can be employed.

Figure 41:
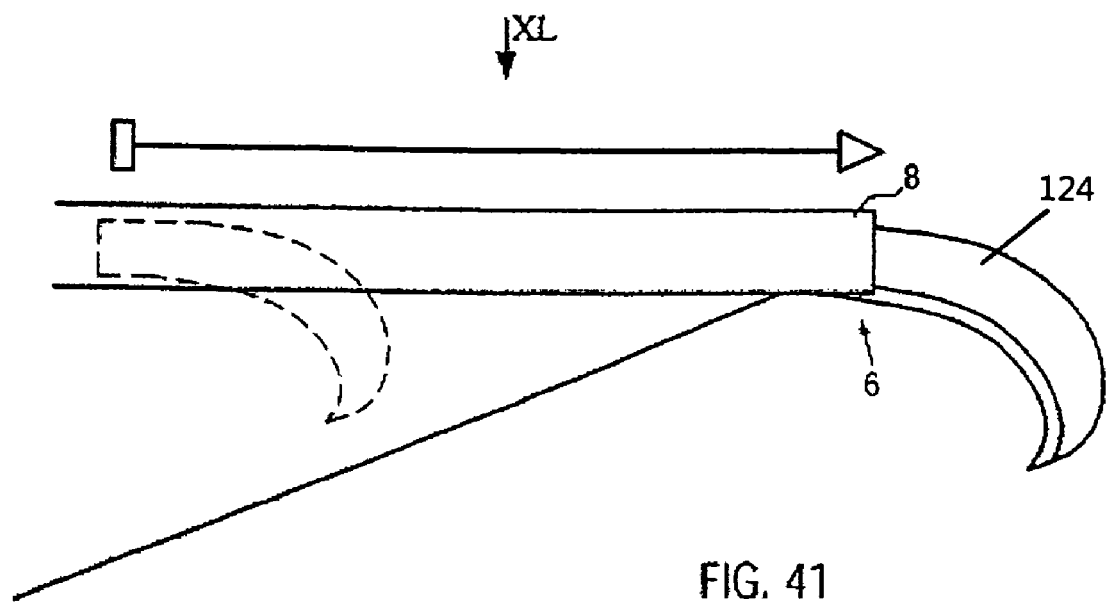
FIG. 41 depicts a schematic representations of modifications of a further embodiment of the manipulator tool according to the invention.
Figure 42:
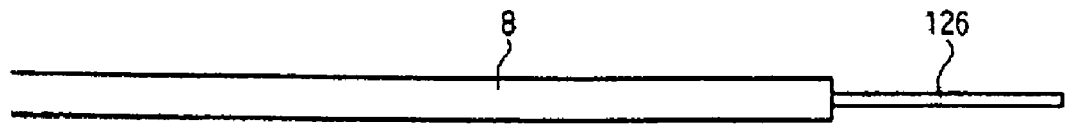
FIG. 42 depicts a schematic representations of modifications of a further embodiment of the manipulator tool according to the invention.
Figure 43:
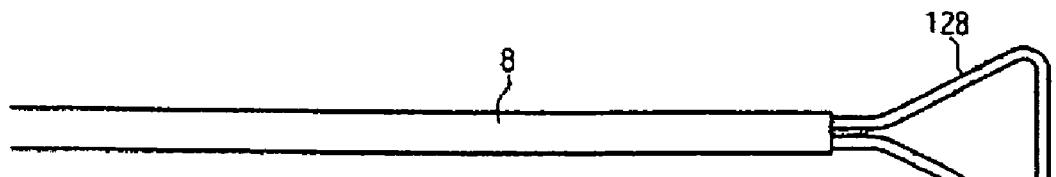
FIG. 43 depicts a schematic representations of modifications of a further embodiment of the manipulator tool according to the invention.

Finally, the at least flexurally stiff cheek 8 itself can be hollow and serve as tool retainer for tools received therein so as to be movable lengthwise. This is represented in FIGS. 41 to 43. For example, tools, such as a blade 124, a needle 126 or a loop 128, can be received in the stiff cheek 8. Of course, fluids can also be passed through, or electrical appliances or optical apparatuses can be received.

Figure 44:
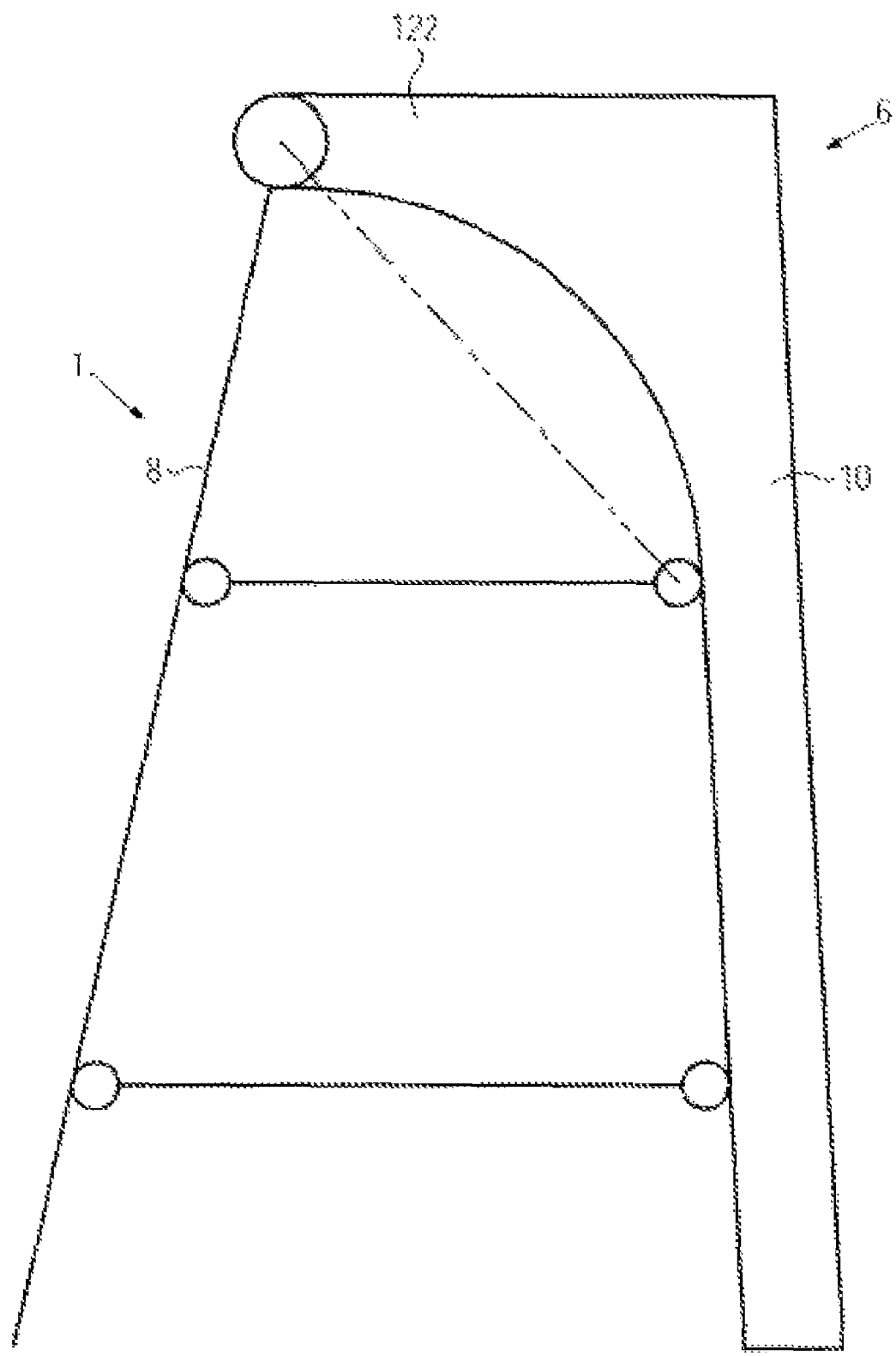
FIG. 44 depicts a schematic representations of modifications of a further embodiment of the manipulator tool according to the invention.

FIG. 44 finally shows that the connection between the cheeks 8 and 10 at the distal end 6 does not have to be wedge-shaped, but can also be embodied to be obtuse by the terminating element 122 which can be, for example, embodied in one piece with the at least flexurally stiff cheek 10. In one or more embodiments, a triangular figure with fixed angles can result at the distal end 6 essentially by the deformation of the manipulator tool 1, which is illustrated by way of example in FIG. 44 by the dot-dash line.

While these embodiments have been described with emphasis on the embodiments, it should be understood that within the scope of the appended claims, the embodiments might be practiced other than as specifically described herein.

What is claimed is:

1. A holding, expanding, or combinations thereof tool comprising at least two jaws opposite one another with respect to a space, wherein at least one jaw is movable with respect to the other jaw, and wherein at least one jaw is formed by a manipulator tool, and wherein the manipulator tool comprises:
   a. a distal end movable in at least one manipulation plane with respect to a proximal end; and
   b. at least two cheeks extending side by side to and spaced apart from each other, wherein the cheeks are flexible at least in the manipulation plane and extend from the proximal end to the distal end, wherein the cheeks are connected between the proximal end and the distal end by at least one at least tension-proof hinge element to permit a shearing movement relative to each other, wherein the cheeks are held at the proximal end at a distance from each other, wherein the one cheek is configured to be at least flexurally stiff and the other cheek to be at least tension-proof, and wherein the at least tension-proof cheek is connected at its distal end to the at least flexurally stiff cheek so as to transmit a pulling force, wherein one cheek is embodied to be driven at the proximal end in the longitudinal direction, wherein the holding, expanding or combinations thereof tool is formed in one piece.

2. The tool of claim 1, wherein the cheek that is embodied to be driven at the proximal end in the longitudinal direction is configured to be tension-proof and flexurally stiff.

3. The tool of claim 1, wherein the at least one jaw that is formed as the manipulator tool further comprises a tool holder disposed at the distal end.

4. The tool of claim 1, wherein the at least one jaw that is formed as the manipulator tool is characterized in that said at least one flexurally stiff cheek comprises a stiffness changing in the direction from the proximal end to the distal end.

5. The tool of claim 1, wherein the hinge elements are arranged around an interior.

6. The tool of claim 1, wherein the space is open towards the distal end.

7. The holding, expanding or combinations thereof tool of claim 1, wherein the at least tension-proof cheek is adjacent to the space.

8. The holding, expanding or combinations thereof tool of claim 1, wherein the at least flexurally stiff cheek or the at least tension-proof cheek are connected to each other at the proximal end.

9. The holding, expanding or combinations thereof tool of claim 8, wherein a coupling element is provided at the point of connection of the proximal end.

10. The holding, expanding or combinations thereof tool of claim 1, wherein each jaw of the holding, expanding or combinations thereof tool is formed by one said manipulator tool.

11. The holding, expanding or combinations thereof tool of claim 1, wherein both cheeks of the manipulator tool are stiff.

12. The holding, expanding or combinations thereof tool of claim 11, wherein said cheeks include inner and outer cheeks, the inner cheeks facing the space having a smaller wall thickness than the outer cheeks.

13. The holding, expanding or combinations thereof tool of claim 1, wherein said cheeks include inner and outer cheeks, the inner cheeks comprising a ribbing transverse to the longitudinal direction.

14. The holding, expanding or combinations thereof tool of claim 1, wherein said cheeks include inner and outer cheeks, the inner cheeks being connected to a tool base via a joint.

* * * * *